United States Patent
Reboud-Ravaux et al.

(10) Patent No.: US 6,355,658 B1
(45) Date of Patent: Mar. 12, 2002

(54) COUMARIN DERIVATIVES, METHODS OF PREPARATION AND APPLICATION AS MEDICINES

(75) Inventors: Michele Reboud-Ravaux, Paris (FR); Lionel Pochet, Gembloux (BE); Caroline Doucet, Paris (FR); Bernard Pirotte, Houpeye (BE); Nicole Boggetto, Yerres (FR); Jacques Delarge, Dolembreux (BE)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 09/445,177

(22) PCT Filed: May 29, 1998

(86) PCT No.: PCT/FR98/01087

§ 371 Date: Feb. 1, 2000

§ 102(e) Date: Feb. 1, 2000

(87) PCT Pub. No.: WO98/55472

PCT Pub. Date: Dec. 10, 1998

(30) Foreign Application Priority Data

Jun. 3, 1997  (FR) ............................................. 97/06814

(51) Int. Cl.⁷ ........................ A61K 31/44; C07D 405/12
(52) U.S. Cl. ..................................... 514/337; 546/282.7
(58) Field of Search ........................ 546/282.7; 514/337

(56) References Cited

U.S. PATENT DOCUMENTS 2,683,720 A    7/1954   Schlesinger ................ 549/287

FOREIGN PATENT DOCUMENTS

EP       0 515 917       12/1992

OTHER PUBLICATIONS

L. Pochet et al., "Esters A.Amides of 6–Chloromethyl–2–oxo–2H–1–Benzopyran–3–Carboxylic Acid as Inhibitors of α–Chymotryp–sin", *Journal of Medicinal Chemistry*, vol. 39, 1996, pp. 2579–2585, XP002053886.

L. Bonsignore et al., "Synthesis and Pharmacological Activity of 2–oxo–(2H) 1–Benzopyran–3–carboxamide Derivatives", *Journal of Heterocyclic Chemistry*, vol. 28, 1993, pp. 517–520, XP002053887.

Chemical Abstracts, vol. 121, No. 27, 1994, p. 1013, XP002053888.

M. Selim, Reactions of 3–Carboethoxy–6–Bromo Coumarins, Chemical Abstracts, vol. 117, No. 27, 1992, p. 811, XP002053889.

M. Moustafa, "Synthesis of Some Coumarin–3 –(4–Aminosulfonyl) Carbanilide Derivatives", Chemical Abstracts, vol. 116, No. 25, 1992, p. 772, XP002053890.

Shah, Sonal "Synthesis of Carboxanilides and amides of 8–Methoycoumarin–3–Carboxilic Acid", Chemical Abstracts, vol. 110, No. 17, 1989, p. 702, XP002053891.

M. El–Kady, "Behavior of 3–(N–P. Tolycarbamido) –6–Bromocoumarins" Chemical Abstracts, vol. 106, No. 19, 1987, p. 666, XP002053892.

M. Agrawal, "Some New Coumarins", Chemical Abstracts, vol. 95, No. 27, 1981, p. 665, XP002053893.

M. Bux, "Coumarins", Chemical Abstracts, vol. 93, No. 5, 1980, p. 211, XP002053894.

D. Seth, "Some New Coumarins", Chemical Abstracts, vol. 93, No. 27, 1980, p. 727, XP002053895.

R. Selleri, "Coumarin Derivatives of Pharmaceutical Interest", Chemical Abstracts, vol. 69, No. 27, 1968, p. 269, XP002053896.

Philadelphia College of Pharmacy and Science, *Remington's Pharmaceutical Sciences*, Mack Publishing Co., 15th Edition, 1975, pp. 465–466.

*Primary Examiner*—Alan L. Rotman
(74) *Attorney, Agent, or Firm*—Young & Thompson

(57) ABSTRACT

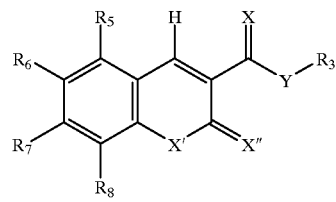

The invention concerns compounds of general formula (I) in which: X, X' and X" independently of each other represent O or S; Y represents O, S, NH or NHS; $R_3$ represents in particular a cycloalkyl group; $R_5$, $R_6$, $R_7$ and $R_8$ mutually identical or different, represent in particular hydrogen; a halogen atom. Said compounds can be used as active substances of medicines as inhibitors of protease.

3 Claims, No Drawings

COUMARIN DERIVATIVES, METHODS OF PREPARATION AND APPLICATION AS MEDICINES

CROSS-REFERENCE

This application is a 371 of PCT/FR98/01087 May 29, 1988 which claims the benefit of French Application 97/06814 Jun. 3, 1997.

The invention relates to novel coumarin derivatives, to processes for preparing them, and to their use as medicinal products which can inhibit serine proteases and cysteine proteases.

The invention applies more particularly to serine or cysteine proteases, such as leukocyte elastase, thrombin, clotting factors (for example IXa, Xa, XIa, XIIa and VIIa), complement factors, plasmin, plasminogen activators (u-PA and t-PA), cathepsin G, acrosin, chymases, tryptases, chymotrypsin, trypsin and cathepsin B.

More specifically, the invention relates to novel coumarin derivatives which can act selectively on a given protease.

Serine protease and cysteine protease are involved in a great many physiological processes. Pathological states can become established when a disequilibrium is observed between the protease and its natural macromolecular inhibitor(s). Low-molecular-weight synthetic inhibitors can be used in this case to counteract excess proteolysis and can thus be of great therapeutic value in the following pathologies: pulmonary emphysema, rheumatoid arthritis, ageing of the skin and inflammation (involvement of leukocyte elastase and cathepsin G); pancreatitis (involvement of pancreatic elastase, chymotrypsin and trypsin): tumor invasion and metastasis (plasmin, plasminogen activators and cathepsin B); thrombosis, cerebral and coronary infarction (involvement of thrombin and clotting factors); thrombolysis and fertility disorders (plasmin and plasminogen activators); attacks by parasites and viruses (some of these organisms produce serine and cysteine proteases).

Among the serine protease inhibitors described in the literature and obtained by total synthesis, modified peptides or compounds of totally non-peptide nature are distinguished (Demuth 1990,*J. Enzym. Inhib.* 3:249–278; Bernstein et al. 1994, in *Progress in Medicinal Chemistry* 31: 59–120). These inhibitors have the advantage of being potentially more stable with respect to in vivo metabolization processes and of optionally being able to be administered orally.

Many classes of synthetic non-peptide compounds which have serine protease inhibitory properties are known from the prior art. Among these, suicide substrates have been prepared, such as haloenol and ynenol lactones (Daniels et al. 1983, *J. Biol Chem.* 258: 15046–15053;Katzenellenbogen et al. 1992, *Bioorg. Med. Chem. Lett.* 2: 1399–1404; Tam et al. 1984, *J. Am. Chem. Soc.* 106: 6849–6851), isocoumarins (Harper et al. 1985, *Biochemistry* 24: 1831–1841; Harper 1985, *Biochemistry* 24: 7200–7213), 3,4-dihydro-6-halomethylcoumarins (Béchet et al. 1973, *Eur. J. Biochem.* 35: 527–539; Mor et al. 1990 *Biochim. Biophys. Acta* 1038: 119–124), functionalized arylcyclopeptides (Reboud-Ravaux et al. 1991, *Boichem. Biophys. Res. Commun.* 178: 352–359; Wakselman et al. 1993, *J. Med. Chem.* 36: 1539–1547) and β-lactams (Doherty et al. 1986, *Nature* 322:192–194; Knight et al. 1992, *Biochemistry* 31: 8160–8170; Maillard et al. 1990, *Eur. J. Biol.* 52: 213–221; Wakselman et al. 1991, *FEBS Lett.* 282: 377–381).

Among these inhibitors of suicide substrate type, halomethyldihydrocoumarins have attracted particular attention. They have shown good inhibitory activity with respect to a large number of serine proteases, in particular including α-chymotrypsin, pig pancreatic elastase, human leukocyte elastase, urokinase and thrombin (Béchet et al. 1973, *Eur. J. Biochem.* 35: 527–539; Béchet et al. 1977, *Biochimie* 59: 231–239; Béchet et al. 1973, *Biochimie* 59: 241–246; Vilain et al. 1991,*Biochim. Biophys. Acta* 1076: 401–405; Reboud-Ravaux et al. 1990, *Biochim. Biophys. Acta* 1038: 119–124). However, these products, which are difficult to synthesize, lack selectivity.

It is of the greatest interest to synthesize protease inhibitors which are specific for a given protease, in order to inhibit this enzyme without acting on nearby proteases.

The present invention relates to the preparation of novel coumarin derivatives which allow this aim to be achieved since they combine activity and specificity.

The invention also relates to the preparation of novel coumarin derivatives whose synthesis is more readily accessible.

The invention relates to compounds corresponding to the general formula (I) below:

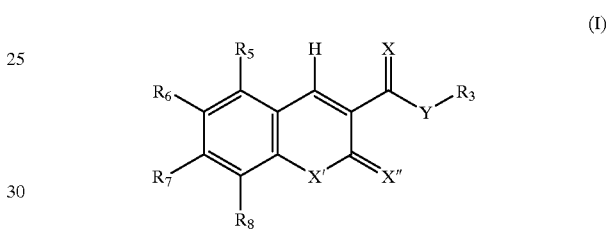

(I)

in which:

X, X' and X", independently of each other, represent O or S,

Y represents O, S, NH or NHS, $R_3$ represents a cycloalkyl group, in particular of 3 to 12 carbon atoms and optionally containing at least one hetero atom chosen from O, S and N, optionally substituted by one or more linear or branched alkyl group(s) of 1 to 6 carbon atoms, an aryl group, in particular a phenyl or naphthyl group optionally substituted by 1 to 7 and in particular 1 to 5 substituents chosen from: a halogen atom; a linear or branched alkyl group of 1 to 6 carbon atoms; a linear or branched alkoxy group of 1 to 6 carbon atoms; a linear or branched alkylthio group of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a perhaloalkyl group of 1 or 2 carbon atoms, in particular —$CF_3$; a hydroxyl group; a mercapto; a nitro group; a cyano group; a carboxylic or carboxamide radical; a linear or branched alkoxycarbonyl group of 1 to 6 carbon atoms; a carbaldehyde group; a sulfonamide group optionally mono- or disubstituted on the nitrogen with 1 or 2 linear or branched hydrocarbon-based chain(s) of 1 to 6 carbon atoms; an amidine or guanidine group;

a 5- to 14-membered, in particular 5- or 6-membered, mono- or polycyclic heteroaryl group containing one or more nitrogen and/or sulfur and/or oxygen atoms, in particular a pyridyl group, optionally substituted by 1 to 6 substituents chosen from: a halogen atom;

a linear or branched alkyl group of 1 to 6 carbon atoms; an aryl group; a linear or branched alkoxy group of 1 to 6 carbon atoms; a linear or branched alkylthio group of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a perhaloalkyl group of 1 or 2 carbon atoms, in particular —$CF_3$; a hydroxyl group; a mercapto group; a nitro group; a cyano group; a carboxylic or carboxamide radical; a linear or branched alkoxycarbonyl group of 1 to 6 carbon atoms; a carbaldehyde group; a sulfonamide group optionally mono- or disubstituted on the nitrogen with 1 or 2 linear or branched hydrocarbon-based chain(s) of 1 to 6 carbon atoms; an amidine or guanidine group, with the proviso that $R_3$ is other than a cycloalkyl group or an aryl group when Y represents NH;

$R_3$ advantageously representing —$C_6H_5$, —$C_6H_4CH_3$, —$C_6H_4I$, —$C_6H_4NO_2$, —$C_6H_4F$, —$C_6H_4Br$, —$C_6H_4Cl$, —$C_6H_4CF_3$, —$C_6H_4OCH_3$, —$C_6H_3Cl_2$, —$C_6H_3ClCH_3$, —$C_6H_3ClOCH_3$,

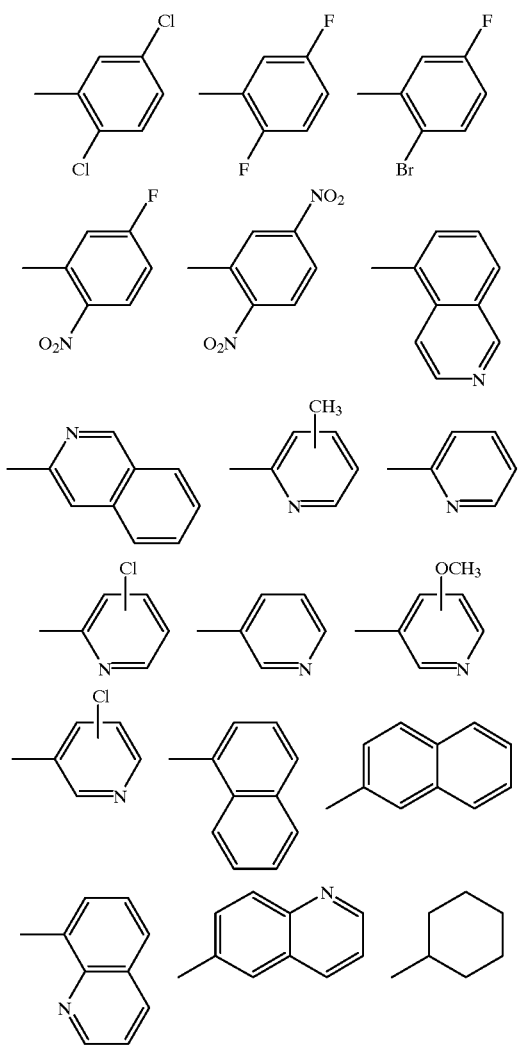
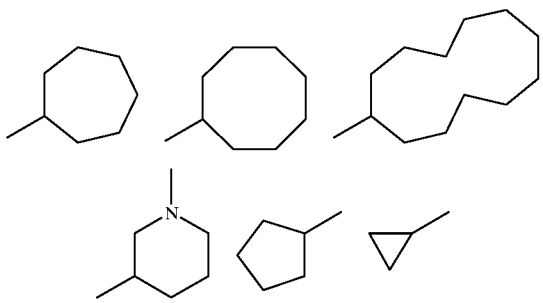

$R_5$, $R_6$, $R_7$ and $R_8$, which may be identical or different, represent hydrogen; a halogen atom; a linear or branched alkyl group of 1 to 6 carbon atoms; a linear or branched haloalkyl group of 1 to 6 carbon atoms, in particular halomethyl and in particular —$CH_2Cl$; a perhaloalkyl group of 1 or 2 carbon atoms, in particular —$CF_3$; a linear or branched alkyl group of 1 to 6 carbon atoms bearing an amine, amidine or guanidine function or a sulfonium function bearing two linear or branched alkyl substituents of 1 to 6 carbon atoms, an aryl or aralkyl group in which the alkyl group contains from 1 to 6 carbon atoms; a carboxylic or carboxamide radical; a linear or branched alkoxycarbonyl group of 1 to 6 carbon atoms; a linear or branched alkoxy group of 1 to 6 carbon atoms; a linear or branched alkylthio group of 1 to 6 carbon atoms; an aralkyl group in which the linear or branched alkyl radical contains from 1 to 6 carbon atoms; an aryl group optionally substituted by one or more groups chosen from halogen, linear or branched alkyl of 1 to 6 carbon atoms or linear or branched alkoxy of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a hydroxyl group; a mercapto group; a nitro group; a cyano group; a sulfonamide group optionally mono- or disubstituted on the nitrogen with 1 or 2 linear or branched hydrocarbon-based chain(s) of 1 to 6 carbon atoms; an amidine or guanidine group; a group —$CH_2$—O— $R_9$, in which $R_9$ represents:
hydrogen;
a linear or branched alkyl group of 1 to 6 carbon atoms; aryl, in particular phenyl or naphthyl optionally substituted by one or more groups chosen from halogen, linear or branched alkyl of 1 to 6 carbon atoms or linear or branched alkoxy of 1 to 6 carbon atoms; arylalkyl of 1 to 6 carbon atoms; $R_{11}C(=O)$—, in which $R_{11}$ represents a linear or branched alkyl group of 1 to 6 carbon atoms, optionally mono- or polyhalogenated, and in particular —$CF_3$;

a group —$CH_2$—S—$R_9$, in which $R_9$ has the meaning given above;

a group —$CH_2NR_{12}R_{13}$, in which $R_{12}$ and $R_{13}$, which may be identical or different, have the meanings given above with regard to $R_9$;

$R_5$, $R_6$, $R_7$ and $R_8$ advantageously representing H—, $ClCH_2$—, $CH_3C(=O)$—O—$CH_2$—, $C_2H_5$—C(=O)—O—$CH_2$—, $(CH_3)_3C$—C(=O)—O—$CH_2$—, $(CH_3)_2CH$—C(=O)—O—$CH_2$—, $CH_3(CH_2)_2$—C(=O)—O—$CH_2$—, $CF_3$—C(=O)—O—$CH_2$, $C_6H_5$—S—$CH_2$—, $NH_2$—$CH_2$—, Br and the salts of organic or inorganic acids or of organic or inorganic bases and the optical isomers of the compounds of formula (I); with the proviso that the following products are excluded:

1)

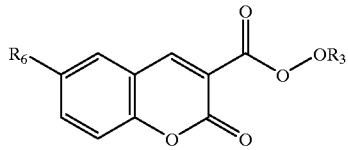

$R_3$ representing $C_6H_5$, $R_6$ representing H or $CH_3$, with the proviso also that:

2) when, in the general formula, X, X', X" and Y represent O and $R_6$ represents —$CH_2Cl$, $R_3$ is other than —$C_6H_5$, —$C_6H_4CH_3$, —$C_6H_4Cl$, —$C_6H_4I$, —$C_6H_4mNO_2$, —$C_6H_3pClmCH_3$, —$C_6H_4mBr$, —$C_6H_4mF$, —$C_6H_4mOCH_3$,

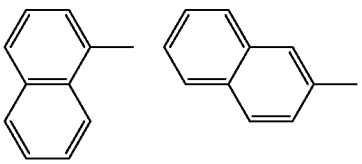

3) when, in the general formula, X, X', X" and Y represent O, and $R_3$ represents —$C_6H_4pCHO$, $R_7$ is other than an alkoxy substituent of 1 to 6 carbon atoms,
4) when, in the general formula, X, X', X" and Y represent O and $R_6$ represents —$C_6H_5$,
(–) $R_3$ is other than —H, —$CH_3$, —$NO_2$, —Cl or —Br when $R_5$, $R_7$ and $R_8$ represent —H,
(–) $R_7$ is other than —Br or —$N(CH_2CH_3)_2$, when $R_5$, $R_6$ and $R_8$ represent —H,
(–) $R_8$ is other than —$OCH_3$ or —$NO_2$ when $R_5$, $R_6$ and $R_7$ represent —H,
5) when, in the general formula, X, X', X" and Y represent O and $R_5$, $R_6$, $R_7$ and $R_8$ represent —H, $R_3$ is other than

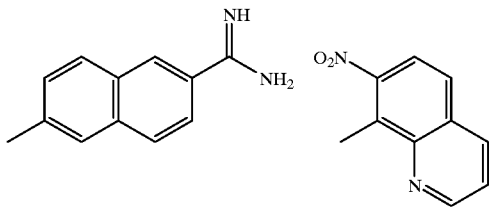

with the proviso also that:
6) when, in the general formula, X, X' and X" represent O, Y represents NH and $R_3$ represents 2-thiazolyl, $R_6$ and $R_8$ are other than —H, —$NO_2$, —Br, —Cl or —I,
7) when, in the general formula, X, X' and X" represent O, Y represents NH and —$R_3$ represents 2-pyridyl,
(–) $R_6$ is other than —$NO_2$, —$NH_2$ or —$NHCOCH_3$ when $R_5$, $R_7$ and $R_8$ represent —H,
(–) $R_7$ is other than —$NO_2$ or —$NH_2$ when $R_8$ represents —H, —OH or —$OCH_3$, and $R_5$ and $R_6$ represent H, 8) when, in the general formula, X, X' and X" represent O, Y represents NH and $R_5$, $R_6$, $R_7$ and $R_8$ represent —H, $R_3$ is other than:

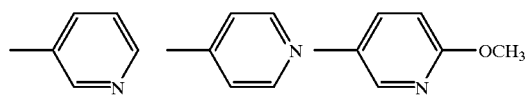

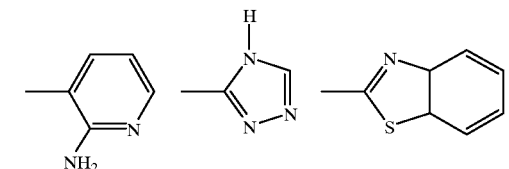

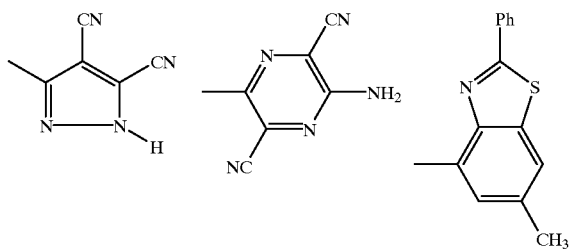

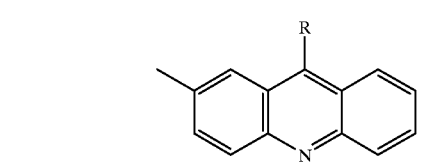

(2-acrinidyl substituted in position 9)]

9) and with the proviso that the following products are excluded:

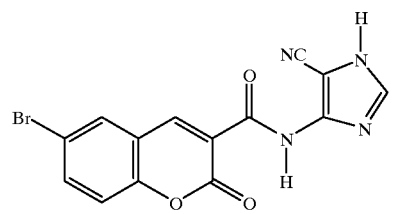

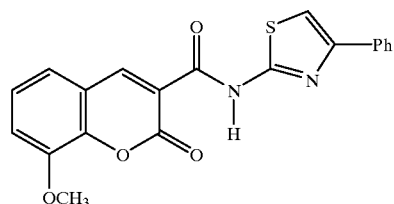

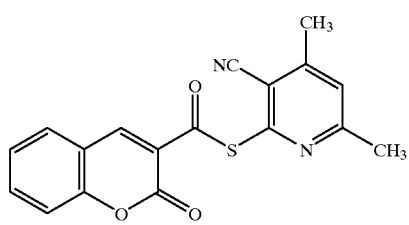

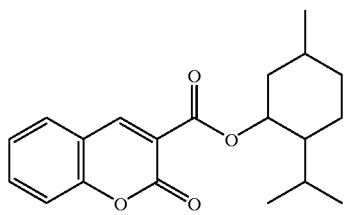

Salts which are preferred according to the invention are physiologically acceptable salts.

By way of example, and in a non-exhaustive manner, mention may be made of the salts of hydrochloric acid, hydrobromic acid, sulfuric acid, phosphoric acid, methanesulfonic acid, toluenesulfonic acid, lactic acid, citric acid, tartaric acid, succinic acid and salts of inorganic bases such as sodium hydroxide, potassium hydroxide, aqueous ammonia and organic bases such as triethylamine and L-lysine.

The invention also relates to compounds corresponding to the following formula:

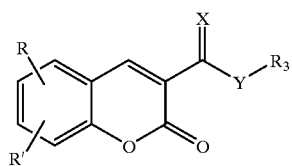

in which $R_3$, X and Y have the meanings given above, R and R' have the same meanings as $R_5$, $R_6$, $R_7$ and $R_8$ as defined above, and in particular R and R' correspond to $R_6$ and $R_8$ respectively.

The invention also relates to compounds corresponding to the following formula:

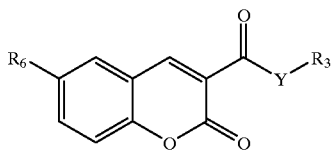

in which
$R_3$ represents
an aryl group, in particular phenyl or naphthyl, optionally substituted by 1 to 7, in particular 1 to 5, substituents chosen from: a halogen atom; a linear or branched alkyl group of 1 to 6 carbon atoms; a linear or branched alkoxy group of 1 to 6 carbon atoms; a linear or branched alkylthio group of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a perhaloalkyl group of 1 or 2 carbon atoms, in particular —$CF_3$; a hydroxyl group; a mercapto group; a nitro group; a cyano group; a carboxylic or carboxamide radical; a linear or branched alkoxycarbonyl group of 1 to 6 carbon atoms; a carbaldehyde group; a sulfonamide group optionally mono- or disubstituted on the nitrogen with 1 or 2 linear or branched hydrocarbon-based chain(s) of 1 to 6 carbon atoms; an amidine or guanidine group;
a 5- to 14-membered, in particular 5- or 6-membered, mono- or polycyclic heteroaryl group containing one or more nitrogen and/or sulfur and/or oxygen atoms, in particular a pyridyl group, optionally substituted by 1 to 6 substituents chosen from: a halogen atom; a linear or branched alkyl group of 1 to 6 carbon atoms; an aryl group; a linear or branched alkoxy group of 1 to 6 carbon atoms; a linear or branched alkylthio group of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a perhaloalkyl group of 1 or 2 carbon atoms, in particular —$CF_3$; a hydroxyl group; a mercapto group; a nitro group; a cyano group; a carboxylic or carboxamide radical; a linear or branched alkoxycarbonyl group of 1 to 6 carbon atoms; a carbaldehyde group; a sulfonamide group optionally mono- or disubstituted on the nitrogen with 1 or 2 linear or branched hydrocarbon-based chain(s) of 1 to 6 carbon atoms; an amidine or guanidine group, with the proviso that $R_3$ is other than an aryl group when Y represents NH;

$R_6$ and Y have the meanings given above.

The invention also relates to compounds corresponding to the following formula:

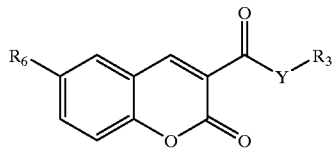

$R_3$ and Y have the meaning given above and $R_6$ has the meaning given above with the exception of $ClCH_2$—.

These compounds are advantageous in the context of their use on pathologies involving elastase.

The invention also relates to compounds corresponding to the following formula:

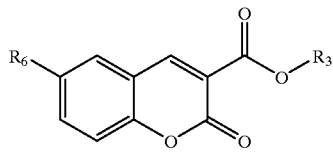

in which
$R_6$ represents H or $CH_3$,
$R_3$ represents $mClC_6H_4$,

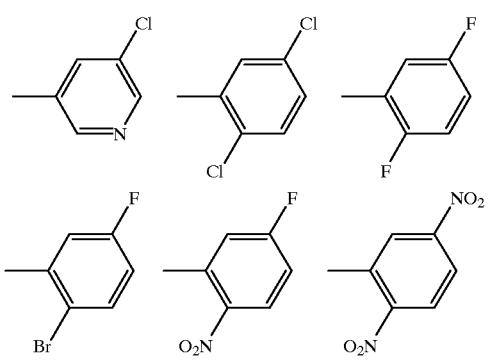

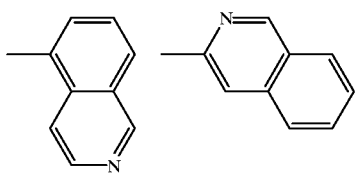
The invention also relates to compounds corresponding to the following formula:
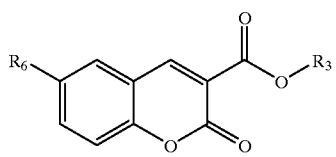
in which $R_6$ represents $ClCH_2$— and $R_3$ is chosen from
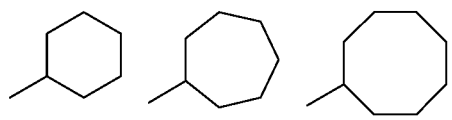
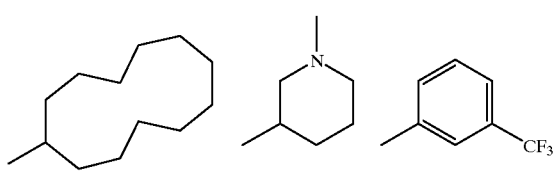
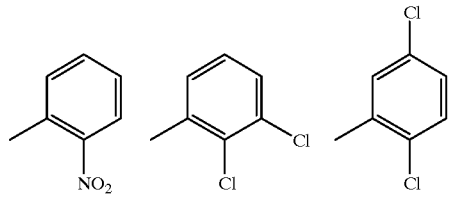
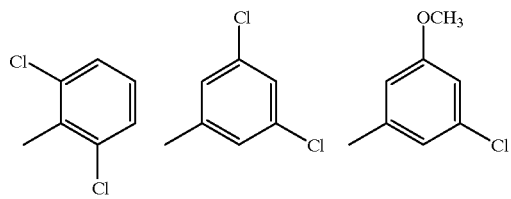
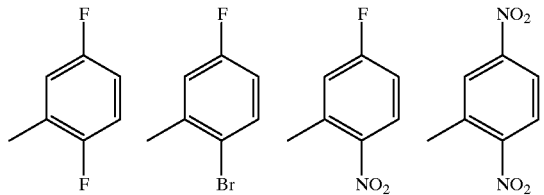
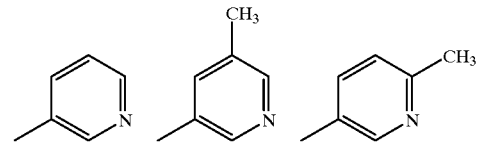
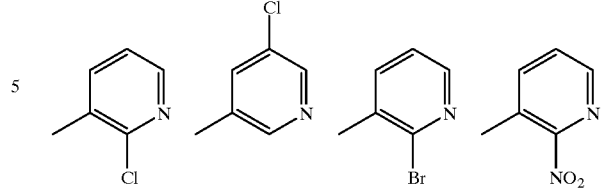
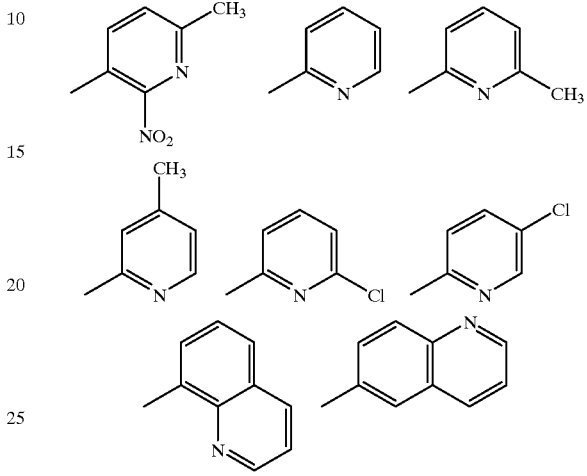
The invention also relates to compounds corresponding to the following formula:
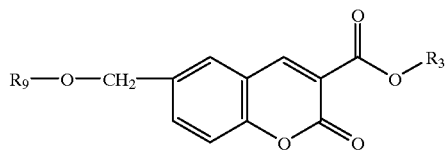
in which $R_9$ represents
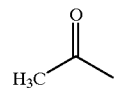
and $R_3$ is chosen from
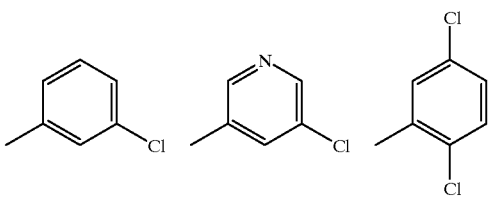
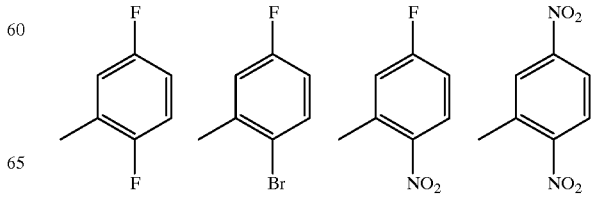

-continued

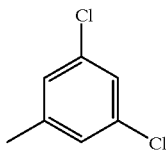

or R₉ represents

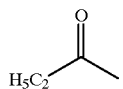

and R₃ is chosen from

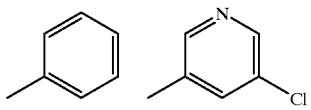

or R₉ represents

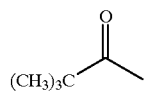

and R₃ represents

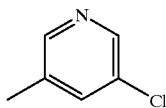

or R₉ represents

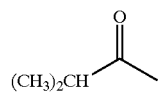

and R₃ represents

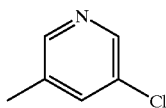

or R₉ represents

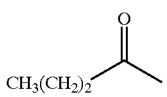

and R₃ represents

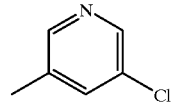

The invention also relates to compounds corresponding to the formula

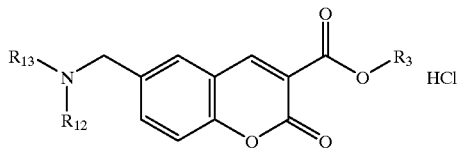

in which R₁₂=R₁₃=H and R₃ represents

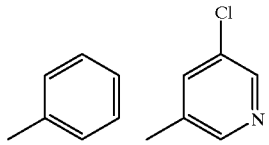

The invention also relates to compounds corresponding to the formula:

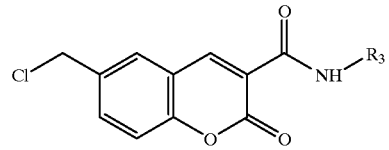

in which R₃ represents

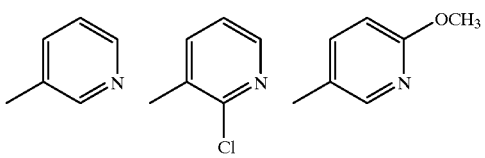

The invention also relates to compounds corresponding to the following formula:

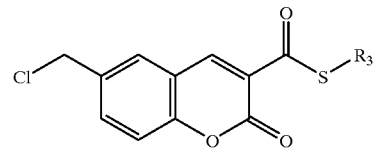

in which R₃ is chosen from:

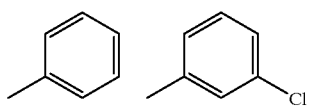

The invention also relates to compounds corresponding to one of the following formulae:

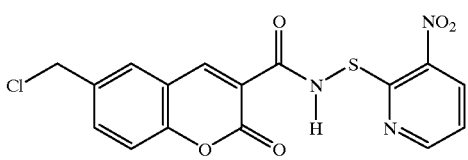

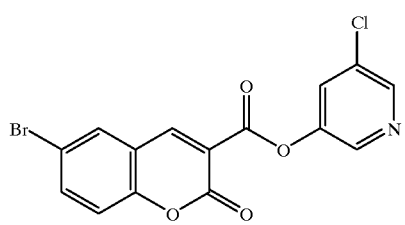

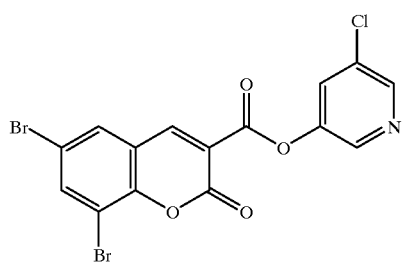

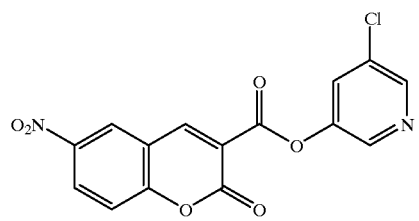

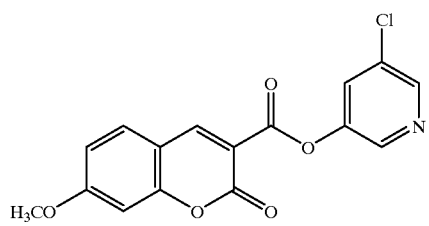

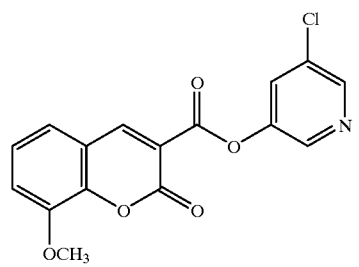

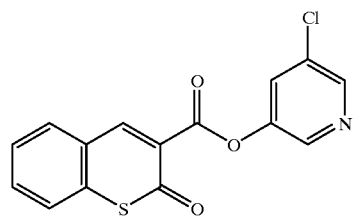

The invention also relates to compounds corresponding to the following formula:

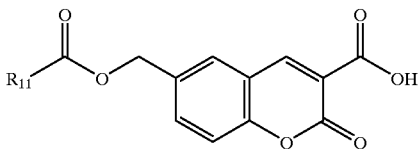

in which:
$R_{11}$=$CH_3$—, $C_2H_5$—, $C_3H_7$—, $(CH_3)_3C$—, $(CH_3)_2CH$— or to the following formula:

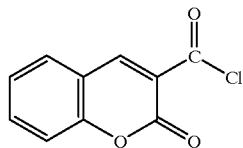

or to the following formula:

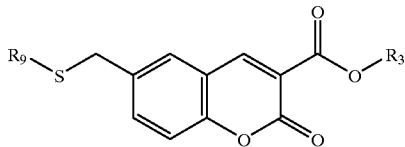

in which $R_3$ represents ethyl and $R_9$ represents phenyl.

The invention also relates to a pharmaceutical composition, characterized in that it comprises, as active substances, at least one of the compounds described above, in combination with a pharmaceutically acceptable vehicle.

The invention also relates to a cosmetic composition, characterized in that it comprises, as active substances, at least one of the compounds described above.

The invention also relates to the use of one of the compounds described above for the preparation of a medicinal product intended for treating pathologies involving serine proteases such as thrombin, chymotrypsin, elastases, cathepsin G, plasminogen activators (u-PA and t-PA), plasmin, tryptases, chymases, cysteine proteases, clotting factors, complement factors, acrosin or kallicrein.

The invention also relates to the use of one of the compounds of the general formula below:

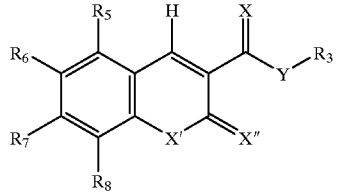

in which:
X, X' and X", independently of each other, represent O or S,
Y represents O, S, NH or NHS,
$R_3$ represents p2 a cycloalkyl group, in particular of 3 to 12 carbon atoms and optionally containing at least one hetero atom chosen from O, S and N, optionally substituted by one or more linear or branched alkyl group(s) of 1 to 6 carbon atoms,
an aryl group, in particular a phenyl or naphthyl group optionally substituted by 1 to 7 and in particular 1 to 5 substituents chosen from: a halogen atom; a linear or branched alkyl group of 1 to 6 carbon atoms; a linear or branched alkoxy group of 1 to 6 carbon atoms; a linear or branched alkylthio group of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a perhaloalkyl group of 1 or 2 carbon atoms, in particular —CF$_3$; a hydroxyl group; a mercapto; a nitro group; a cyano group; a carboxylic or carboxamide radical; a linear or branched alkoxycarbonyl group of 1 to 6 carbon atoms; a carbaldehyde group; a sulfonamide group optionally mono- or disubstituted on the nitrogen with 1 or 2 linear or branched hydrocarbon-based chain(s) of 1 to 6 carbon atoms; an amidine or guanidine group;

a 5- to 14-membered, in particular 5- or 6-membered, mono- or polycyclic heteroaryl group containing one or more nitrogen and/or sulfur and/or oxygen atoms, in particular a pyridyl group, optionally substituted by 1 to 6 substituents chosen from: a halogen atom; a linear or branched alkyl group of 1 to 6 carbon atoms; an aryl group; a linear or branched alkoxy group of 1 to 6 carbon atoms; a linear or branched alkylthio group of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a perhaloalkyl group of 1 or 2 carbon atoms, in particular —CF$_3$; a hydroxyl group; a mercapto group; a nitro group; a cyano group; a carboxylic or carboxamide radical, a linear or branched alkoxycarbonyl group of 1 to 6 carbon atoms; a carbaldehyde group; a sulfonamide group optionally mono- or disubstituted on the nitrogen with 1 or 2 linear or branched hydrocarbon-based chain(s) of 1 to 6 carbon atoms; an amidine or guanidine group, R$_3$ advantageously representing —C$_6$H$_5$, —C$_6$H$_4$CH$_3$, —C$_6$H$_4$I, —C$_6$H$_4$NO$_2$, —C$_6$H$_4$F, —C$_6$H$_4$Br, —C$_6$H$_4$Cl, —C$_6$H$_4$CF$_3$, —C$_6$H$_4$OCH$_3$, —C$_6$H$_3$Cl$_2$, —C$_6$H$_3$ClCH$_3$, —C$_6$H$_3$ClOCH$_3$,

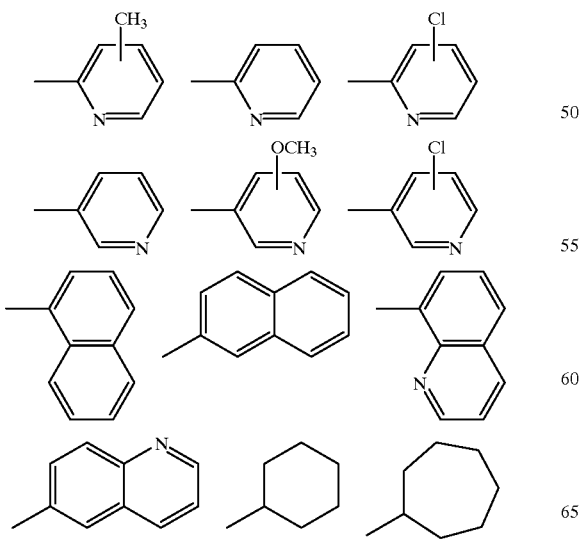

-continued

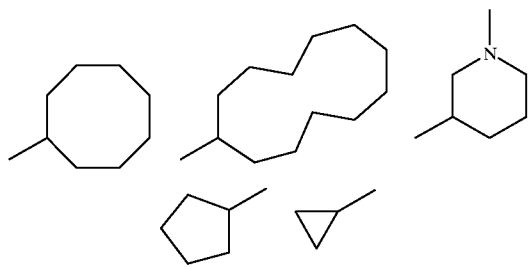

R$_5$, R$_6$, R$_7$ and R$_8$, which may be identical or different, represent hydrogen; a halogen atom; a linear or branched alkyl group of 1 to 6 carbon atoms; a linear or branched haloalkyl group of 1 to 6 carbon atoms, in particular halomethyl and in particular —CH$_2$Cl; a perhaloalkyl group of 1 or 2 carbon atoms, in particular —CF$_3$; a linear or branched alkyl group of 1 to 6 carbon atoms bearing an amine, amidine or guanidine function or a sulfonium function bearing two linear or branched alkyl substituents of 1 to 6 carbon atoms, an aryl or aralkyl group in which the alkyl group contains from 1 to 6 carbon atoms; a carboxylic or carboxamide radical; a linear or branched alkoxycarbonyl group of 1 to 6 carbon atoms; a linear or branched alkoxy group of 1 to 6 carbon atoms; a linear or branched alkylthio group of 1 to 6 carbon atoms; an aralkyl group in which the linear or branched alkyl radical contains from 1 to 6 carbon atoms; an aryl group optionally substituted by one or more groups chosen from halogen, linear or branched alkyl of 1 to 6 carbon atoms or linear or branched alkoxy of 1 to 6 carbon atoms; an amino group optionally substituted by 1 or 2 linear or branched hydrocarbon-based chain(s) of 1 to 6 carbon atoms; a linear or branched acylamino group of 1 to 6 carbon atoms; a hydroxyl group; a mercapto group; a nitro group; a cyano group; a sulfonamide group optionally mono- or disubstituted on the nitrogen with 1 or 2 linear or branched hydrocarbon-based chain(s) of 1 to 6 carbon atoms; an amidine or guanidine group; a group —CH$_2$—O—R$_9$, in which R$_9$ represents:
hydrogen;
a linear or branched alkyl group of 1 to 6 carbon atoms; aryl, in particular phenyl or naphthyl. optionally substituted by one or more groups chosen from halogen, linear or branched alkyl of 1 to 6 carbon atoms or linear or branched alkoxy of 1 to 6 carbon atoms; arylalkyl of 1 to 6 carbon atoms; R$_{11}$C(═O)—, in which R$_{11}$ represents a linear or branched alkyl group of 1 to 6 carbon atoms, optionally mono- or polyhalogenated, and in particular —CF$_3$;

a group —CH$_2$—S—R$_9$, in which R$_9$ has the meaning given above;

a group —CH$_2$NR$_{12}$R$_{13}$, in which R$_{12}$ and R$_{13}$, which may be identical or different, have the meanings given above with regard to R$_9$;

R$_5$, R$_6$, R$_7$ and R$_8$ advantageously representing H—, ClCH$_2$—, CH$_3$C(═O)—O—CH$_2$, C$_2$H$_5$—C(═O)—O—CH$_2$—, (CH$_3$)$_3$C—C(═O)—O—CH$_2$—, (CH$_3$)$_2$CH—C(═O)—O—CH$_2$—, CH$_3$(CH$_2$)$_2$—C(═O)—O—CH$_2$—, CF$_3$—C(═O)—O—CH$_2$, C$_6$H$_5$—S—CH$_2$—, NH$_2$—CH$_2$—, Br and the salts of organic or inorganic acids or of organic or inorganic bases and the optical isomers of the compounds of formula (I); for the preparation of a medicinal product intended for treating pathologies involving thrombin, cathepsin G, plasminogen activators, plasmin, tryptase, chymase or cysteine proteases.

The invention also relates to the use of a compound of formula:

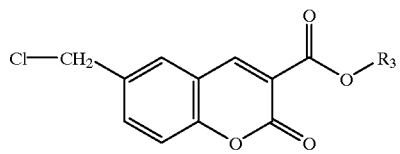

in which $R_3$ represents an aryl group substituted by one or more halogens, $NO_2$, an alkyl radical of 1 to 6 carbon atoms or an alkoxy radical of 1 to 6 carbon atoms, for the preparation of a medicinal product intended for treating pathologies involving thrombin.

The processes described below can be used to prepare the compounds of the invention.

A general method for synthesizing esters, thioesters, amides and N-[aryl/alkyl]sulfanylamides of substituted 2-oxo-2H-1-benzopyran-3-carboxylic acids is as follows.

The ethyl esters of 2-oxo-2H-1-benzopyran-3-carboxylic acids can be obtained from the appropriate salicylaldehyde following the methods described in L. Pochet et al., J. Med. Chem. 1996, 39: 2579–2585 and in the examples of the present patent application (see later).

This synthesis can be illustrated by the following reaction scheme:

in which R" represents $R_3$ defined above and R represents $R_5$, $R_6$, $R_7$ and/or $R_8$ described above, (i) ethyl malonate; (ii) HCl/H$_2$O/EtOH; (iii) SOCl$_2$; (iv) R"OH or R"SH or R"NH$_2$ or R"SNH$_2$/pyridine/dioxane One method for synthesizing esters, thioesters and amides of substituted 2-oxo-2H-1-benzothiopyran-3-carboxylic acids is as follows.

The ethyl esters of 2-oxo-2H-1-benzothiopyran-3-carboxylic acids can be prepared according to the method described in O. Meth Cohn and Tarnowski B., Synthesis, 1978, 1: 56–58 (i→iii below). The subsequent steps are based on the methods described in L. Pochet et al., J. Med. Chem. 1996, 39: 2579–2585, and in the examples of the present patent application (iv→vi below).

This synthesis can be illustrated by the reaction scheme below:

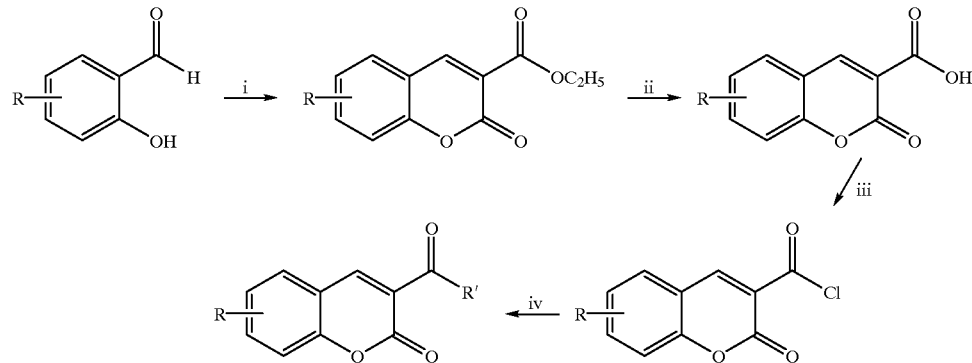

R'=OR", SR", NHR", NHSR"

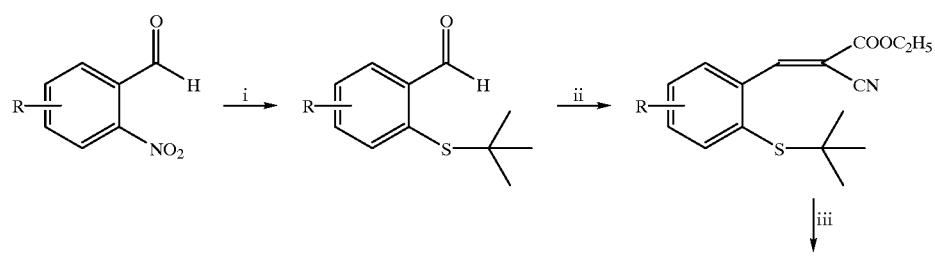

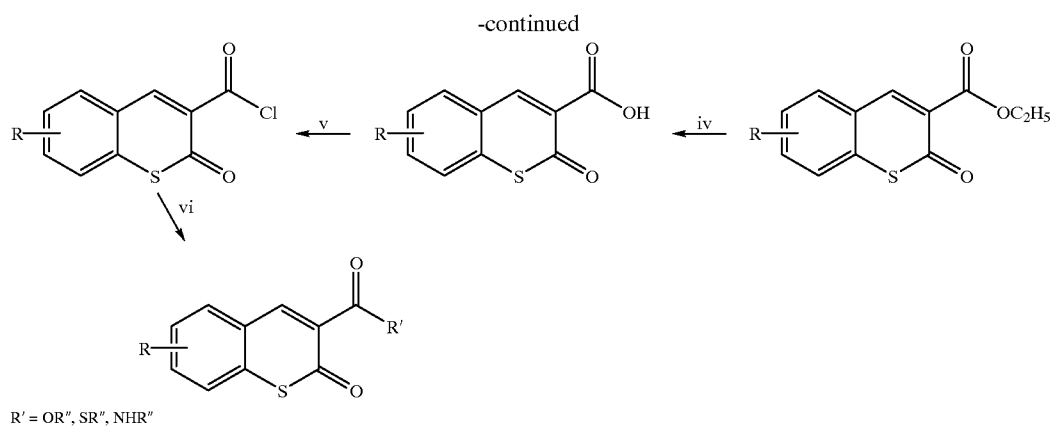

R' = OR", SR", NHR"

in which R" represents $R_3$ defined above and R represents $R_5$, $R_6$, $R_7$ and/or $R_8$ described above, (i) t-$C_4H_9$SH/DMF; (ii) ethyl cyanoacetate; (iii) polyphosphoric acid; (iv) HCl/$H_2$O/EtOH; (v) SOCl$_2$; (vi) R"OH or R"SH or R"NH$_2$/pyridine/dioxane.

One method for synthesizing esters, thioesters and amides of substituted 2-oxo-2H-1-benzopyran-3-carbothioic acids is as follows.

The o-ethyl esters of 2-oxo-2H-1-benzopyran-3-carbothioic acids can be prepared according to the method described in B. S. Kirkiacharian and A. Danan, Synthesis, 1986, 5: 383–5 and in G. Barnikow and Stickmann G., Chem. Ber., 1967, 100: 1428–1435 (step i). The subsequent steps are based on the methods described in L. Pochet et al., J. Med. Chem. 1996, 39: 2579–2585 and in the examples of the present patent application.

This synthesis can be illustrated by the reaction scheme below:

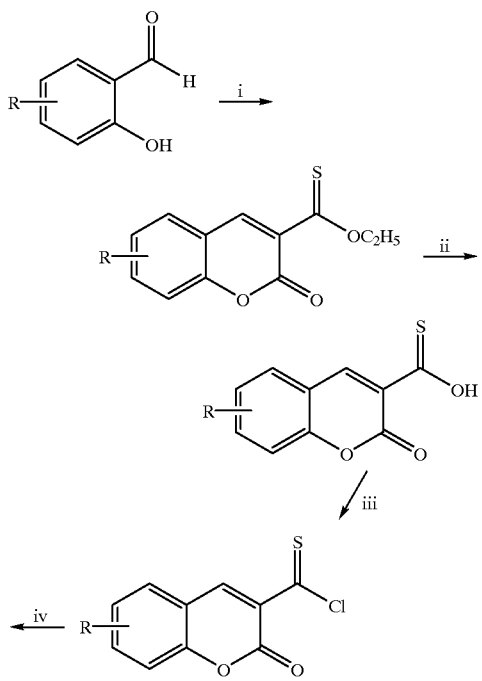

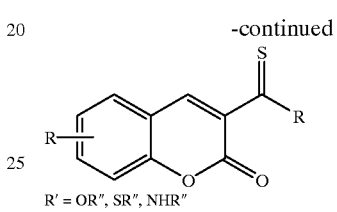

R' = OR", SR", NHR"

in which R' represents $R_3$ defined above and R represents $R_5$, $R_6$, $R_7$ and/or $R_8$ described above, (i) ethyl monothiomalonate; (ii) HCl/$H_2$O/EtOH; (iii) SOCl$_2$; (iv) R"OH or R"SH or R"NH$_2$/pyridine/dioxane.

One method for synthesizing esters, thioesters and amides of substituted 2-thioxo-2H-1-benzopyran-3-carboxylic acids is as follows:

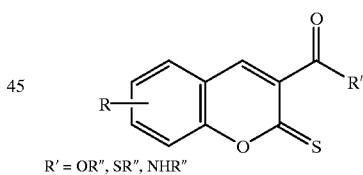

R' = OR", SR", NHR"

in which R' represents $R_3$ defined above and R represents $R_5$, $R_6$, $R_7$ and/or $R_8$ described above.

The ethyl esters of 2-thioxo-2H-1-benzopyran-3-carboxylic acids can be prepared according to the method described in Shishido Tadao and Okada Hisashi, Jpn. Kokai Tokkyo Koho JP 02,172,916. The subsequent steps are based on the methods described in L. Pochet et al., J. Med. Chem. 1996, 39: 2579–2585 and in the examples of the present patent application.

One method for synthesizing esters, thioesters and amides of substituted 2-thioxo-2H-1-benzopyran-3-carbothioic acids is as follows.

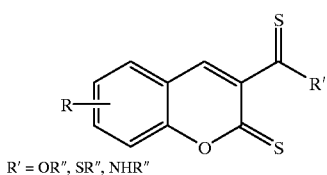

R' = OR", SR", NHR"

in which R" represents $R_3$ defined above and R represents $R_5$, $R_6$, $R_7$ and/or $R_8$ described above.

The o-ethyl esters of 2-thioxo-2H-1-benzopyran-3-carbothioic acids can be prepared according to the method described in A. Avetisyan et al., Khim. Geterosilk. Soedin., 1996, 7:909–912. The subsequent steps are based on the methods described in L. Pochet et al., J. Med. Chem. 1996, 39: 2579–2585 and in the examples of the present patent application.

The coumarin derivatives of the invention can be used in the preparation of pharmaceutical compositions.

These pharmaceutical compositions can be in the form of solutions, suspensions, powders or soluble granules, syrups or elixirs, ear drops, nose drops or eye drops, tablets, gelatin capsules, aerosols, ointments, transcutaneous or suppository applications, in dosed presentations containing non-toxic supports, adjuvants and excipients. The injections can be, for example, intravenous, intramuscular, subcutaneous, intradermal, intrasternal, intraperitoneal or intra-articular. It is also possible to use infusion or instillation methods (for example intratracheal methods).

In order to target the pulmonary tissue more particularly, solutions containing albumin microspheres to which the coumarin derivatives are bound covalently can be produced.

The preparations for oral use can comprise one or more sweeteners, dyes, flavorings and preserving agents. The tablets contain the coumarin-based active molecule according to the invention mixed with non-toxic pharmaceutically acceptable excipients. Examples of excipients are inert diluents, such as calcium or sodium carbonate, calcium or sodium phosphate and lactose; granulating and disintegrating agents, for example corn starch; binders, for example gelatin, starch and gum arabic; and lubricants, for example talc or magnesium stearate. The tablets can be coated or uncoated (for example using glyceryl monostearate or distearate) in order to delay the disintegration and absorption.

The preparation can be contained in a solid gelatin capsule containing the active molecule mixed with an inert solid (for example calcium carbonate or phosphate, or kaolin), or in a soft gelatin capsule. in which the coumarin derivative is mixed with water or fatty substances (for example liquid paraffin, olive oil or groundnut oil).

Aerosols of three types in particular can be envisaged: (a) aqueous aerosols (administered using atomizers) for which better solubilization of the coumarin derivative can be obtained by adding a co-solvent or formation of micelles; (b) pressurized aerosols whose vector gases are, for example, chloro- or fluorohydrocarbons of various formulae (or a substitute product) in which the coumarin derivative may be dissolved or in suspension; (c) aerosols in powder form with the coumarin derivative as fine particles, for example in a gelatin capsule.

Aqueous suspensions containing the coumarin derivative and the appropriate excipients can be produced, optionally with one or more preserving agents (for example ethyl p-hydroxybenzoate), dyes, sweeteners and flavorings. Among the excipients, mention may be made of suspending agents (for example methylcellulose and gum arabic), dispersants and wetting agents such as natural phosphatides (for example lecithin) or products for condensing ethylene oxide with various partially esterified fatty acids or aliphatic alcohols. Oily suspensions of the active molecule can be prepared using a plant oil (for example olive oil, groundnut oil, sesame oil, coconut oil or soybean oil) or a mineral oil (for example liquid paraffin), optionally in the presence of sweeteners and flavorings such as those mentioned above, as well as preserving agents (in particular an antioxidant such as ascorbic acid).

Syrups or elixirs may contain sweeteners (for example sucrose or sorbitol), one or more preserving agents and flavorings. Granules or powders, which may be suspended in water, can be obtained by mixing the coumarin derivative with a wetting agent or dispersant, one or more preserving agents and various excipients. Emulsions of the coumarin derivative in water can be produced using a mineral oil (for example liquid paraffin) or a plant oil (olive oil or groundnut oil) and various emulsifiers, such as natural gums (gum arabic), natural phosphatides (lecithin) and various fatty acids, which may or may not be partially esterified, or condensation products of these partial esters with ethylene oxide. The emulsions can also contain flavorings and sweeteners.

The coumarin derivative according to the invention can also be in the form of aqueous or oily, injectable sterile suspensions using wetting or suspending agents such as those described above. The solvents, diluents or excipients can be, for example, 1,3-butanediol, an isotonic sodium chloride solution, a Ringer solution, water, aqueous solutions of dextrose and similar sugars, ethanol or glycols, etc. Suppositories containing the active principle can be prepared with conventional excipients such as polyethylene glycol or, for example, cocoa butter. For local uses, it is possible to prepare ointments, creams, jellies, suspensions, solutions, etc. containing the active principle. This can be carried out by preparing a solution of the active principle in a solvent which is known to promote transdermal absorption, such as ethanol or dimethyl sulfoxide (DMSO) with or without excipient. Local administration will preferably be carried out by means of a patch of porous reservoir-membrane type or of solid matrix type. Other transdermal administration systems such as those described in U.S. Pat. Nos. 3,742,951, 3,797,494, 3,966,934, 4,031,894 and 3,921,636 are also applicable.

Doses of from 0.01 to 50 mg/kg/day are appropriate. However, the dose for a given patient may depend upon a certain number of factors, such as, for example, the efficacy of the coumarin derivative considered, the age, weight, route and frequency of administration, the dietary regime, medicinal interactions and the seriousness of the complaint.

These compositions may be used in particular for treating a great many pathologies in which an excess of protease is involved.

This is the case in particular for coumarin derivatives which behave like inhibitors of leukocyte elastase and of cathepsin G. They can be used in the treatment of acute or chronic inflammatory processes or the treatment of degenerative processes, irrespective of the organ involved, such as pulmonary emphysema, inflammation of the bronchi, rheumatoid arthritis, infectious arthritis, osteoarthritis, spondylarthritis, rheumatic fever, periodontitis, gingivitis, arteriosclerosis, glomerulonephritis, respiratory distress syndrome, septic shock, Crohn's disease, gout, pancreatitis, microvascular hemorrhage, mucoviscidosis, lupus erythematosus, psoriasis, respiratory insufficiency, idiopathic pulmonary fibrosis, chronic infections of the respiratory pathways, ischemia re-infusion syndrome and the phenomena of invasion and diffusion of malignant cells and similar diseases.

Thrombin inhibitors can be useful as anticoagulants or antithrombotic agents, in particular in the treatment of stable and unstable angina, diseases of thrombotic origin and/or which give rise to thrombotic complications (for example thrombophlebitis) and in the treatment and prevention of myocardial infarction and venous and arterial thrombosis.

Inhibitors of plasminogen activators or plasmid activators can be used in particular in the treatment of tumoral invasion and metastases, controlling thrombolysis and fertility, in various clotting disorders (deep vein thrombosis, coronary diseases), in various inflammatory processes (rheumatoid arthritis, psoriasis, leprosy, transplant rejection), in cicatrization, liver disorders and various infections.

Inhibitors of mastocyte tryptases and kinases can be used in the treatment of allergic responses and psoriasis.

Inhibition of cysteine proteases (for example cathepsin B) with the coumarin derivatives can lead to applications in tumoral invasion and the metastasic process.

The coumarin-based active principle can also be used in the composition of cosmetic preparations such as creams, ointments, lotions, gels, milks, etc. They may thus be continuous systems (aqueous, oily or solid solutions) or dispersed systems (emulsions or suspensions). In particular, the coumarin derivative may be contained in liposomes. Hylanes (hyaluronane derivatives) and various polymeric systems (polyol prepolymers, microspheric systems, etc.) can also be used as vehicles for the active principle.

Examples of such compositions are:

| Cream | |
| --- | --- |
| coumarin-based active principle | 0.01–5% (m/m) |
| cetyl alcohol | 15 g |
| 1000° cetomacrogol | 3 g |
| glycerol | 5 g |
| aqua conservans | 77 g |

(Comment: 1000° cetomacrogol=polyoxymethylenated cetostearyl alcohol aqua conservans=0.07% (m/v) methyl p-aminobenzoate (NIPANGINE) 0.03% (m/v) propyl p-aminobenzoate (NIPASOL) in distilled water)

| Ointment | |
| --- | --- |
| coumarin-based active principle | 0.01–5% (m/m) |
| petroleum jelly | |

| Lotion | |
| --- | --- |
| coumarin-based active principle | 0.01–5% (m/m) |
| cetyl alcohol | 2.4 g |
| 1000° cetomacrogol | 2.4 g |
| sweet almond oil | 2.4 g |
| cetiol V° | 2.4 g |
| glycerol | 2.4 g |
| aqua conservans q.s. | 80 g |

(Comment: cetiol V°=decyl oleate)

| Gel | |
| --- | --- |
| coumarin-based active principle | 0.01–5% (m/m) |
| carbopol 940 | 2% |
| NaOH q.s. | pH 6.0 |
| aqua conservans | |

The anti-elastase action of the coumarin derivatives can also lead to applications in cosmetology, in particular in the field of solar erythema, the topical treatment of inflammation and ageing of the skin. The active principle can be included, for example, in creams, lotions, tonics, body milks, etc.

EXAMPLES

Synthesis of the Intermediates

Example 1

Synthesis of 5-methylsalicylaldehyde 28.8 g of p-cresol (0.26 mol) are dissolved in 100 ml of water in a round-bottomed flask containing 80 g of NaOH. The mixture is heated to 60–65° C. and 40.5 ml of $CHCl_3$ (0.51 mol) are added in several portions over a period of 30 to 40 min. The mixture is refluxed for 1 h and then cooled. The excess chloroform is removed by distillation under reduced pressure. The medium is acidified with dilute $H_2SO_4$ and then subjected to vapor entrainment. The distillate collected (±500 ml) is extracted with ether. The solvent is removed by distillation under reduced pressure. The residue is taken up in 100 ml of saturated sodium bisulfite solution. After vigorous stirring for 2 h, followed by leaving to stand for 1 h, the bisulfite adduct precipitated is collected by filtration and washed with ether. The bisulfite combination is decomposed by heating on a water bath in dilute $H_2SO_4$ for 30 min. The aldehyde is extracted with ether. The ether solution is dried over $MgSO_4$. The solvent is removed under reduced pressure. The residue is recrystallized from ethanol.

(L. Pochet et al., J. Med. Chem. 1996, 39: 2579–2585)

Example 2

Synthesis of 6-methyl-2-oxo-2H-1-benzopyran-3-carboxylic acid 2 g of 5-methylsalicylaldehyde (14.7 mmol), 3.06 g of malonic acid (29.4 mmol), 1.3 g of pyridine and 0.08 g of aniline are dissolved in a minimum amount of ethanol. The mixture is heated at 40° C. on a water bath for 6 h. Next, it is diluted with water, acidified and then extracted with ether. The solvent is removed by distillation under reduced pressure. The residue obtained is recrystallized from ethanol.

(L. Pochet et al., J. Med. Chem. 1996, 39: 2579–2585)

Example 3

Synthesis of 5-hydroxymethylsalicylaldehyde

A mixture of 9 ml of salicylaldehyde (84.46 mmol), 17 ml of aqueous 37% formaldehyde solution (~200 mmol) and 42 ml of concentrated HCl is heated on a water bath at 80° C. with stirring for 20 min. After cooling, the supernatant is removed by settling of the phases and the residual pink crystalline mass is taken up in 200 ml of boiling water. The suspension obtained is refluxed for 30 min. The supernatant is separated out after settling and placed at +4° C. to bring about crystallization of the final product. A further 200 ml of boiling water are added to the residual oil and the suspension is refluxed for 30 min. The supernatant is added to the first decantate. After cooling, the product is collected by filtration, washed with water and dried. It is then recrystallized from chloroform.

(L. Pochet et al., J. Med. Chem. 1996, 39: 2579–2585; R. Stoermer and K. Behn, Ber. 1901, 34: 2455–2460)

Example 4

Synthesis of Ethyl 6-hydroxymethyl-2-oxo-2H-1-benzopyran-3-carboxylate 30 g of 5-hydroxymethylsalicylaldehyde (197 mmol), 34.8 g of diethyl nmalonate (217 mmol), 2.5 ml of piperidine, 1 ml of acetic acid and 100 ml of ethanol are placed in a round-bottomed flask. The mixture is refluxed for 17 h. 250 ml of boiling water are added to the hot suspension and the reaction medium is then placed at +4° C. The precipitate obtained is collected by filtration and washed twice with a methanol/water mixture (6:4, v/v, 200 ml) and then dried. It is optionally recrystallized from ethanol.

(L. Pochet et al., J. Med. Chem. 1996, 39: 2579–2585)

Using the same operating conditions but starting with 5-nitrosalicylaldehyde, 4-methoxysalicylaldehyde and 3-methoxysalicylaldehyde gives ethyl 6-nitro-2-oxo-2H-1-benzopyran-3-carboxylate, ethyl 7-methoxy-2-oxo-2H-1-benzopyran-3-carboxylate and ethyl 8-methoxy-2-oxo-2H-1-benzopyran-3-carboxylate, respectively.

Example 5

Synthesis of Ethyl 6-chloromethyl-2-oxo-2H-1-benzopyran-3-carboxylate

A mixture of 1 g of ethyl 6-hydroxymethyl-2-oxo-2H-1-benzopyran-3-carboxylate (3.9 mmol) and 10 ml of thionyl chloride is refluxed for 3 h. The solution obtained is evaporated under reduced pressure. The residue is re-suspended in 10 ml of dry toluene and the solvent is evaporated off under reduced pressure. The last two steps are repeated twice. The residue obtained is taken up in chloroform and the organic phase is washed three times with 0.1 N HCl solution and then dried over MgSO$_4$. The solvent is removed by distillation under reduced pressure and the residue is recrystallized from CHCl$_3$/Petroleum ether.

(L. Pochet et al., J. Med. Chem. 1996, 39: 2579–2585)

Example 6

Synthesis of 6-hydroxymethyl-2-oxo-2H-1-benzopyran-3-caxboxylic Acid 20 g of ethyl 6-hydroxymethyl-2-oxo-2H-1-benzopyran-3-carboxylate (78 mmol) are dissolved in 350 ml of boiling ethanol. 2000 ml of 3 N HCl are added slowly to this boiling solution. The mixture is kept boiling for 3 h in an open vessel. After cooling, the precipitate obtained is filtered off and washed with water. The product is optionally recrystallized from an ethanol/water mixture (1/5 v/v).

Example 7

General Method for Synthesizing Acyloxymethyl-2-oxo-2H-1-benzopyran-3-carboxylic Acids A. 3 g of 6-hydroxymethyl-2-oxo-2H-1-benzopyran-3-carboxylic acid (13.62 mmol) and 30 ml of the appropriate anhydride are refluxed for 2 h. After cooling, 200 ml of water are added and the suspension is stirred for 1 h. The precipitate obtained is collected by filtration, washed with water and dried. The product is dissolved in the minimum amount of chloroform and 40/60 petroleum ether is added. The precipitated product is collected by filtration, washed with petroleum ether and dried.

B. A mixture of 3 g of 6-hydroxymethyl-2-oxo-2H-1-benzopyran-3-carboxylic acid (13.62 mmol), 30 ml of dry dioxane, the appropriate acid chloride (27.24 mmol) and pyridine (27.24 mmol) is stirred at room temperature for 60 min. The solvent is removed by distillation under reduced pressure and the residue obtained is re-dissolved in chloroform. The organic phase is washed three times with 0.1 N HCl solution and then dried over MgSO$_4$. The solvent is removed by distillation under reduced pressure and the residue is recrystallized from a suitable solvent such as acetonitrile, chloroform or ethyl acetate.

Example 8

Synthesis of Alkyl or Aryl 6-hexamethylenetetraammoniomethyl-2-oxo-2H-1-benzopyran-3-carboxylate Chlorides 1.5 equivalents of hexamethylenetetramine are added to 2 g of the appropriate alkyl or aryl 6-chloromethyl-2-oxo-2H-1-benzopyran-3-carboxylate dissolved in 20 ml of chloroform and the solution is refluxed for 3 h. If the reaction is not complete, an additional 0.5 equivalent of hexamethylenetetramine is added and refluxing is continued for 1 h. The hexaminium salt precipitate is collected by filtration, washed with chloroform and dried.

Example 9

Synthesis of 2-oxo-2H-1-benzothiopyran-3-carboxylic Acid

Ethyl 2-oxo-2H-1-benzothiopyran-3-carboxylate, obtained according to the method described in O. Meth Cohn and Tarnowski (Synthesis, 1978, 1, 56–58), is hydrolyzed under the conditions described in Example 6 to give the title product. The product is isolated under the same conditions as in Example 6.

Example 10

General Method for Synthesizing 2-oxo-2H-1-benzopyran-3-carboxylic Acids by Alkaline Hydrolysis of the Ethyl Esters A suspension of 2 g of ethyl 2-oxo-2H-1-benzopyran-3-carboxylate (variously substituted in positions 5, 6, 7 and 8) in 60 ml of 10% NaOH is refluxed for 10–30 min. After cooling, the solution is adjusted to pH 1 by addition of 12 N HCl. The white precipitate obtained is collected by filtration, washed with water and recrystallized from ethanol or acetonitrile.

Example 11

Synthesis of the Final Products

General method for synthesizing esters, thioesters, amides and N-(aryl/alkyl)sulfanylamides of 2-oxo-2H-1-benzopyran-3-carboxylic acid (Ia1-8), of 6-methyl-2-oxo-2H-1-benzopyran-3-carboxylic acid (Ib1-8), of 6-chloromethyl-2-oxo-2H-1-benzopyran-3-carboxylic acid (Ic'1-5; Ic"1-11; Ic'''1-13; Ic''''1-2; II1-3, III1-2, IV1), of 6-acyloxymethyl-2-oxo-2H-1-benzopyran-3-carboxylic acids (Id 2, 3, 5, 6, 8, 9, 10, 11–16) of 6-bromo-, 6,8-dibromo-, 6-nitro-, 7-methoxy- and 8-methoxy-2-oxo-2H-1-benzopyran-3-carboxylic acids (Ig1, Ih1, Ii1, Ij1, Ik1) and of 2-oxo-2H-1-benzothiopyran-3-carboxylic acid (V1).

1 g of the appropriate carboxylic acid and 10 ml of thionyl chloride are refluxed for 3 h. The solution obtained is evaporated under reduced pressure. The residue is suspended in 10 ml of dry toluene. The solvent is removed by distillation under reduced pressure. The final two steps are repeated twice. The residue is dispersed in 10 ml of dioxane. The appropriate alcohol, thiol or amine (1.1 eq) and anhydrous pyridine (1.1 eq) are added to this suspension. After stirring for 30 to 90 min at room temperature, the solvent is removed by distillation under reduced pressure. The residue is dissolved in chloroform and the organic phase is washed three times with 0.1 N HCl solution and then dried over $MgSO_4$. The solvent is evaporated off under reduced pressure and the residue obtained is recrystallized from a suitable solvent such as ethyl acetate, chloroform, propanol, acetone, acetonitrile, ethyl acetate/petroleum ether or chloroform/petroleum ether, or is washed with methanol.

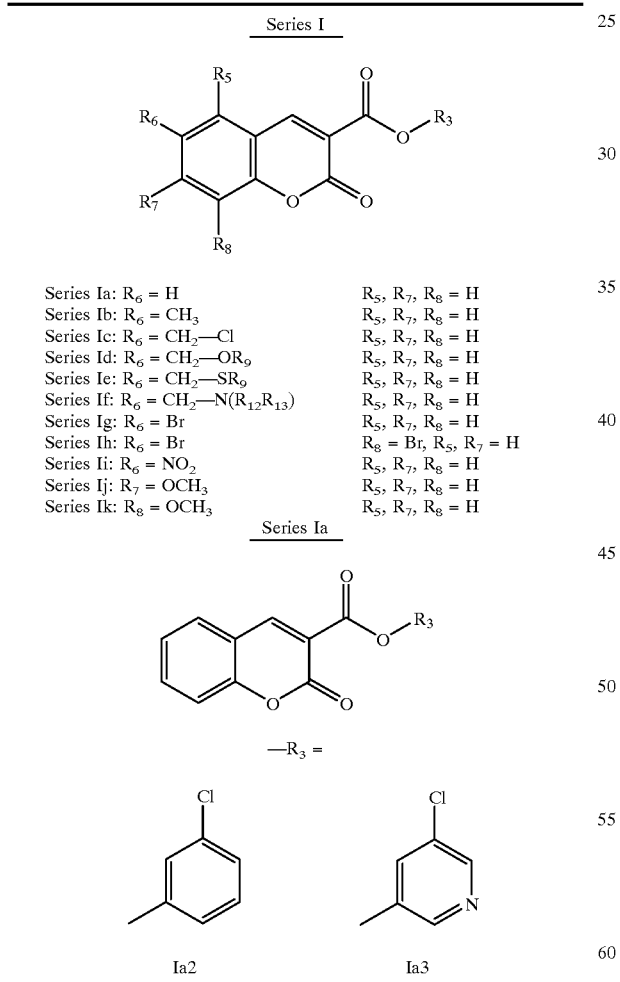

Ia2: 3-chlorophenyl 2-oxo-2H-1-benzopyran-3-carboxylate m.p.=170–171° C.

Ia3: 5-chloro-3-pyridyl 2-oxo-2H-1-benzopyran-3-carboxylate m.p.=208–209° C., NMR ($CDCl_3$/TMS): δ(ppm) 7.10 to 7.80 (m, 6H, 5-H, 6-H, 7-H, 8-H, 4'-H), 8.50 (bs, 2H, 2'-H, 6'-H), 8.70 (s, 1H, 4-H)

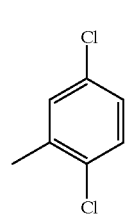

Ia4

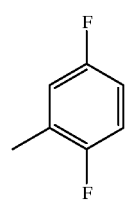

Ia5

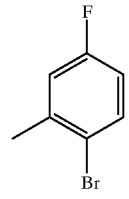

Ia6

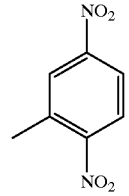

Ia7

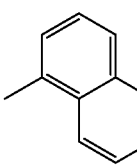

Ia8

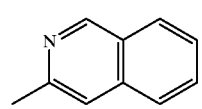

Ia9

Ia10

Ia4: 2,5-dichlorophenyl 2-oxo-2H-1-benzopyran-3-carboxylate m.p.=189–192° C.; IR (KBr): 3105, 1779, 1726, 1609, 1563, 1203 $cm^{-1}$ Ia5: 2,5-difluorophenyl 2-oxo-2H-1-benzopyran-3-carboxylate m.p.=134–137° C.; IR (KBr): 3086, 3051, 1777, 1728, 1610, 1568, 1501, 1238, 1209 cm$^{-1}$ Ia6: 2-bromo-5-fluorophenyl 2-oxo-2H-1-benzopyran-3-carboxylate m.p.=173–175° C.; IR (KBr): 3094, 1773, 1723, 1609, 1564, 1476, 1239, 1202 cm$^{-1}$ Ia7: 5-fluoro-2-nitrophenyl 2-oxo-2H-1-benzopyran-3-carboxylate m.p.=219–223° C.; IR (KBr): 3117, 3094, 1777, 1720, 1611, 1598, 1565, 1526, 1344, 1280, 1241, 1203 cm$^{-1}$ Ia8: 2,5-dinitrophenyl 2-oxo-2H-1-benzopyran-3-carboxylate m.p.=223–225° C.; IR (KBr): 3104, 3049, 1779, 1721, 1611, 1544, 1349, 1198 cm$^{-1}$ Ia9: 5-isoquinolyl 2-oxo-2H-1-benzopyran-3-carboxylate m.p.=190–193° C.; IR (KBr): 3066, 1765, 1716, 1607, 1566, 1373, 1299, 1215 cm$^{-1}$ Ia10: 3-isoquinolyl 2-oxo-2H-1-benzopyran-3-carboxylate m.p.=160–163° C.; IR (KBr): 3066, 3029, 1762, 1723, 1608, 1567, 1380, 1238, 1210 cm$^{-1}$ Series Ib

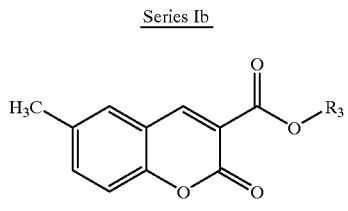

—R$_3$ =

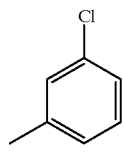
Ib1

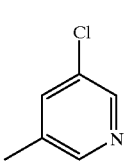
Ib2

Ib1: 3-chlorophenyl 6-methyl-2-oxo-2H-1-benzopyran-3-carboxylate m.p.=175–176° C.

Ib2: 5-chloro-3-pyridyl 6-methyl-2-oxo-2H-1-benzopyran-3-carboxylate m.p.=215–217° C., NMR (CDCl$_3$/TMS): δ(ppm) 2.20 (s, 3H, —CH$_3$), 7.20 to 7.80 (m, 4H, 5-H, 7-H, 8-H, 4'-H), 8.45 (bs, 2H, 2'-H, 6'-H), 8.70 (s, 1H, 4-H)

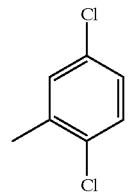
Ib3

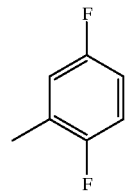
Ib4

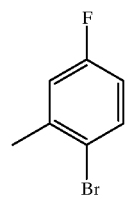
Ib5

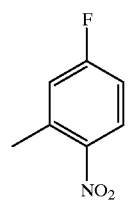
Ib6

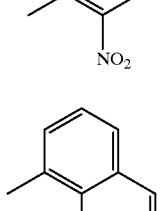
Ib7

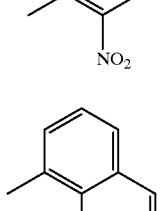
Ib8

Ib3: 2,5-dichlorophenyl 6-methyl-2-oxo-2H-1-benzopyran-3-carboxylate m.p.=175–179° C.; IR (KBr): 309.4, 2928, 1774, 1738, 1621, 1575, 1229, 1205 cm$^{-1}$ Ib4: 2,5-difluorophenyl 6-methyl-2-oxo-2H-1-benzopyran-3-carboxylate m.p.=155–159° C.; IR (KBr): 3061, 2924, 1783, 1768, 1724, 1621, 1573, 1509, 1250, 1209 cm$^{-1}$ Ib5: 2-bromo-5-fluorophenyl 6-methyl-2-oxo-2H-1-benzopyran-3-carboxylate m.p.=187–190° C.; IR (KBr): 3095, 3053, 2927, 1777, 1739, 1621, 1572, 1479, 1239, 1213 cm$^{-1}$ Ib6: 5-fluoro-2-nitrophenyl 6-methyl-2-oxo-2H-1-benzopyran-3-carboxylate m.p.=224–226° C.; IR (KBr): 3114, 3080, 1774, 1718, 1615, 1599, 1572, 1528, 1343, 1239, 1208 cm$^{-1}$ Ib7: 2,5-dinitrophenyl 6-methyl-2-oxo-2H-1-benzopyran-3-carboxylate m.p.=225–229° C.; IR (KBr): 3113, 3079, 3045, 1779, 1723, 1623, 1573, 1547, 1350, 1209 cm$^{-1}$ Ib8: 5-isoquinolyl 6-methyl-2-oxo-2H-1-benzopyran-3-carboxylate m.p.=188–190° C.; IR (KBr): 3067, 1756, 1713, 1620, 1573, 1372, 1220 cm$^{-1}$ Series Ic

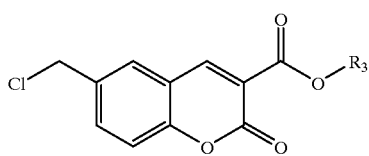

series Ic': $R_3$=cycloalkyl
series Ic'': $R_3$=mono-, polysubstituted phenyl
series Ic''': $R_3$=mono-, polysubstituted pyridyl
seriesIc'''': $R_3$=other aryls Series Ic'

—$R_3$ =

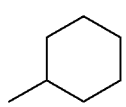 Ic'1

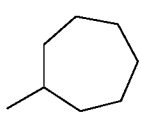 Ic'2

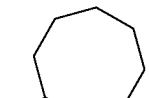 Ic'3

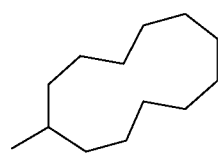 Ic'4

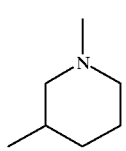 Ic'5

Ic'1: cyclohexyl 6-chloromethyl-2-oxo-2H-1-benzopyran-3-carboxylate m.p.=185–186° C.; IR (KBr): 3064, 2939, 2860, 1743 (C=O ester), 1712 (C=O lactone), 1628, 1586, 1274, 1256 cm$^{-1}$ Ic'2: cycloheptyl 6-chloromethyl-2-oxo-2H-1-benzopyran-3-carboxylate m.p.=171–174° C.; IR (KBr): 3062, 2932, 2855, 1743 (C=O ester), 1708 (C=O lactone), 1628, 1580, 1273, 1256 cm$^{-1}$ Ic'3: cyclooctyl 6-chloromethyl-2-oxo-2H-1-benzopyran-3-carboxylate m.p.=169–170° C.; IR (KBr): 3061, 2925, 2853, 1742 (C=O ester), 1708 (C=O lactone), 1627, 1580, 1274, 1256 cm$^{-1}$ Ic'4: cyclododecyl 6-chloromethyl-2-oxo-2H-1-benzopyran-3-carboxylate m.p.=164–167° C.; IR (KBr): 3051, 2928, 1747 (C=O ester), 1699 (C=O lactone), 1623, 1578, 1475, 1304, 1272, 1255 cm$^{-1}$ $^{Ic'}$5: 1-methyl-3-piperidyl 6-chloromethyl-2-oxo-2H-1-benzopyran-3-carboxylate m.p.=217° C., dec., IR (KBr): 3058, 2940, 2778, 1742 (C=O ester), 1714 (C=O lactone), 1630, 1581, 1273, 1255 cm$^{-1}$ Series Ic''

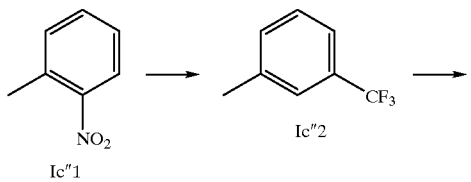

Ic''1: 2-nitrophenyl 6-chloromethyl-2-oxo-2H-1-benzopyran-3-carboxylate m.p.=163–164° C.; IR (KBr): 3077 (aromatic C—H), 1768 (C=O ester), 1727 (C=O lactone), 1609, 1576, 1548, 1374, 1349, 1242, 1204 cm$^{-1}$ Ic''2: 3-trifluoromethylphenyl 6-chloromethyl-2-oxo-2H-1-benzopyran-3-carboxylate m.p.=162–163° C.; IR (KBr): 3069 (aromatic C—H), 1772 (C=O ester), 1756 (C=O lactone), 1621, 1574, 1336, 1239, 1223, 1200 cm$^{-1}$

—$R_3$ =

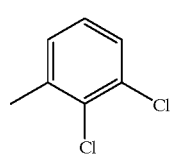 Ic''3

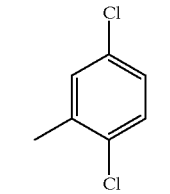 Ic''4

Ic"5

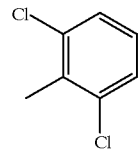

Ic"6

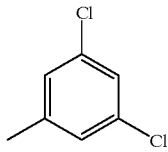

Ic"7

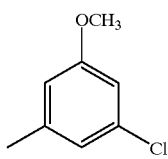

Ia"3: 2,3-dichlorophenyl 6-chloromethyl-2-oxo-2H-1-benzopyran-3-carboxylate m.p.=173–174° C.

Ia"4: 2,5-dichlorophenyl 6-chloromiethyl-2-oxo-2H-1-benzopyran-3-carboxylate m.p.=197–199° C.

Ic"5: 2,6-dichlorophenyl 6-chloromethyl-2-oxo-2H-1-benzopyran-3-carboxylate m.p.=177–178° C.

Ic"6: 3,5-dichlorophenyl 6-chloromethyl-2-oxo-2H-1-benzopyran-3-carboxylate m.p.=208–209° C.

Ic"7: 3-chloro-5-methoxyphenyl 6-chloromethyl-2-oxo-2H-1-benzopyran-3-carboxylate m.p.=184–185° C.; IR (KBr): 3064 (aromatic C—H), 1779 (C=O ester), 1758 (C=O lactone), 1621, 1573, 1377, 1242, 1222, 1150; NMR (CDCl$_3$/HMDS): δ(ppm) 3.72 (s, 3H, —OCH$_3$), 4.57 (s, 2H, —CH$_2$Cl), 6.6 to 6.9 (m, 3H, 2'-H, 4'-H, 6'-H), 7.30 (d, 1H, 8-H), 7.60 (s, 1H, 5-H), 7.65 (d, 1H, 7-H), 8.6 to (s, 1H, 4-H)

Ic"8

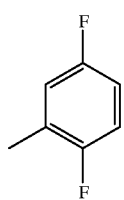

Ic"9

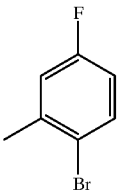

Ic"10

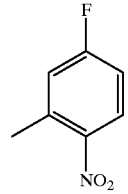

Ic"11

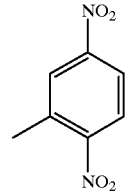

Ic"8: 2,5-difluorophenyl 6-chloromethyl-2-oxo-2H-1-benzopyran-3-carboxylate m.p.=137–140° C.; IR (KBr): 3067, 1782, 1765, 1720, 1622, 1574, 1509, 1250, 1238, 1221 cm$^{-1}$ Ic"9: 2-bromo-5-fluorophenyl 6-chloromethyl-2-oxo-2H-1-benzopyran-3-carboxylate m.p.=203–205° C.; IR (KBr): 3099, 1776, 1724, 1623, 1574, 1481, 1244, 1211 cm$^{-1}$ Ic"10: 5-fluoro-2-nitrophenyl 6-chloromethyl-2-oxo-2H-1-benzopyran-3-carboxylate m.p.=205–208° C.; IR (KBr): 3110, 1777, 1720, 1617, 1598, 1571, 1535, 1276, 1238, 1205 cm$^{-1}$ Ic"11: 2,5-dinitrophenyl 6-chloromethyl-2-oxo-2H-1-benzopyran-3-carboxylate m.p.=153–157° C.; IR (KBr): 3113, 3049, 1780, 1623, 1574, 1548, 1350, 1207 cm$^{-1}$ Series Ic'''

—R$_3$ =

Ic'''1

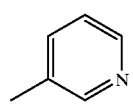

Ic'''2

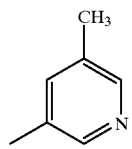

-continued

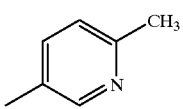 Ic'''3

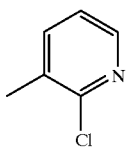 Ic'''4

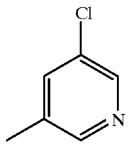 Ic'''5

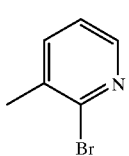 Ic'''6

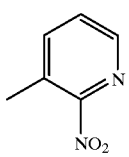 Ic'''7

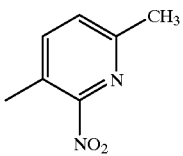 Ic'''8

Ic'''1: 3-pyridyl 6-chloromethyl-2-oxo-2H-1-benzopyran-3-carboxylate m.p.=210° C., dec.; IR (KBr): 3067 (aromatic C—H), 1774 (C=O ester), 1757 (C=O lactone), 1620, 1573, 1215 cm⁻¹; NMR (CDCl₃/TMS): δ(ppm) 4.60 (s, 2H, —CH₂Cl); 7.10 to 7.80 (m, 5H, 5-H, 7-H, 8-H, 4'-H, 5'-H), 8.40 to 8.60 (m, 2'-H, 6'-H), 8.70 (s, 1H, 4-H)

Ic'''2: 5-methyl-3-pyridyl 6-chloromethyl-2-oxo-2H-1-benzopyran-3-carboxylate m.p.=211° C., dec.

Ic'''3: 6-methyl-3-pyridyl 6-chloromethyl-2-oxo-2H-1-benzopyran-3-carboxylate m.p.=205–208° C.; NMR (CDCl₃/TMS): δ(ppm) 2.55 (s, 3H, —CH₃), 4.60 (s, 2H, —CH₂Cl), 7.10 to 7.80 (m, 5H, 5-H, 7-H, 8-H, 4'-H, 5'-H), 8.40 (bm, 1H, 2'-H), 8.60 (s, 1H, 4-H)

Ic'''4: 2-chloro-3-pyridyl 6-chloromethyl-2-oxo-1-benzopyran-3-carboxylate m.p.=198–200° C.; NMR (CDCl₃/TMS): δ(ppm) 4.65 (s, 2H, —CH₂Cl), 7.10 to 7.80 (m, 5H, 5-H, 7-H, 8-H, 4'-H, 5'-H), 8.55 (d, 1H, 6'-H), 8.75 (s, 1H, 4-H)

Ic'''5: 5-chloro-3-pyridyl 6-chloromethyl-2-oxo-2H-1-benzopyran-3-carboxylate m.p.=195–198° C.; NMR (CDCl₃/TMS): δ(ppm) 4.60 (s, 2H, —CH₂Cl), 7.10 to 7.80 (m, 4H, 5-H, 7-H, 8-H, 4'-H), 8.45 (bs, 2H, 2'-H, 6'-H), 8.65 (s, 1H, 4-H)

Ic'''6: 2-bromo-3-pyridyl 6-chloromethyl-2-oxo-2H-1-benzopyran-3-carboxylate m.p.=197–199° C.; NMR (CDCl₃/TMS): δ(ppm) 4.65 (s, 2H, —CH₂Cl), 7.20 to 7.80 (m, 5H, 5-H, 7-H, 8-H, 4'-H, 5'-H), 8.35 (d, 1H, 6'-H), 8.85 (s, 1H, 4-H)

Ic'''7: 2-nitro-3-pyridyl 6-chloromethyl-2-oxo-2H-1-benzopyran-3-carboxylate m.p.=190–193° C.; NMR (CDCl₃/TMS): δ(ppm) 4.60 (s, 2H, —CH₂Cl), 7.05 to 8.00 (m, 5H, 5-H, 7-H, 8-H, 4'-H, 5'-H), 8.55 (d, 1H, 6'-H), 8.75 (s, 1H, 4-H)

Ic'''8: 6-methyl-2-nitro-3-pyridyl 6-chloromethyl-2-oxo-2H-1-benzopyran-3-carboxylate m.p.=203–208° C.; NMR (CDCl₃/TMS): δ(ppm) 2.7 (s, 3H, —CH₃), 4.60 (s, 2H, —CH₂Cl), 7.10 to 7.95 (m, 5H, 5-H, 7-H, 8-H, 4'-H, 5'-H), 8.70 (s, 1H, 4-H)

—R₃ =

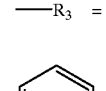 Ic'''9

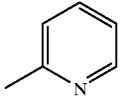 Ic'''10

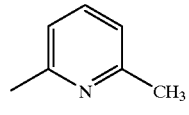 Ic'''11

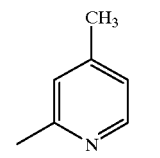 Ic'''12

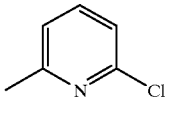 Ic'''13

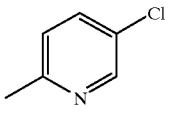

Ic'''9: 2-pyridyl 6-chloromethyl-2-oxo-2H-1-benzopyran-3-carboxylate m.p.=125–129° C.; IR (KBr): 3051 (aromatic C—H), 1736 (C=O, ester and lactone), 1621, 1577, 1245, 1198 cm⁻¹

Ic'''10: 6-methyl-2-pyridyl 6-chloromethyl-2-oxo-2H-1-benzopyran-3-carboxylate m.p.=160–162° C.; NMR CDCl₃/TMS): δ(ppm) 2.60 (s, 3H, —CH₃), 4.60 (s, 2H, —CH₂Cl), 6.90 to 7.90 (m, 6H, 5-H, 7-H, 8-H, 3'-H, 4'-H, 5'-H), 8.80 (s, 1H, 4-H)

Ic'''11: 4-methyl-2-pyridyl 6-chloromethyl-2-oxo-2H-1-benzopyran-3-carboxylate m.p.=152–154° C.

Ic'''12: 6-chloro-2-pyridyl 6-chloromethyl-2-oxo-2H-1-benzopyran-3-carboxylate m.p.=172–173° C.; NMR (CDCl$_3$/TMS): δ(ppm) 4.60 (s, 2H, —CH$_2$Cl), 7.10 to 8 (m, 6H, 5-H, 7-H, 8-H, 3'-H, 4'-H, 5'-H), 8.75 (s, 1H, 4-H)

Ic'''13: 5-chloro-2-pyridyl 6-chloromethyl-2-oxo-2H-1-benzopyran-3-carboxylate m.p.=171–172° C.; NMR (CDCl$_3$/TMS): δ(ppm) 4.60 (s, 2H, —CH$_2$Cl), 7.10 to 7.95 (m, 5H, 5-H, 7-H, 8-H, 3'-H, 6'-H), 8.35 (d, 1H, 4'-H), 8.75 (s, 1H, 4-H)

Series Ic''''

—R$_3$ =

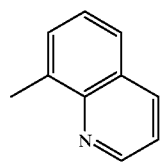

Ic''''1

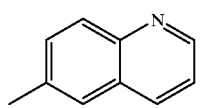

Ic''''2

Ic''''1: 8-quinolyl 6-chloromethyl-2-oxo-2H-1-benzopyran-3-carboxylate m.p.=127° C., dec.

Ic''''2: 6-quinolyl 6-chloromethyl-2-oxo-2H-1-benzopyran-3-carboxylate m.p.=205–208° C.

Series Id

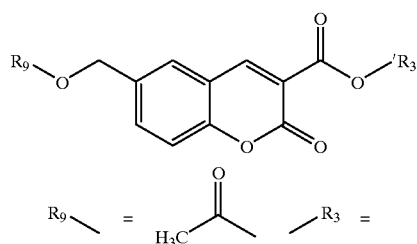

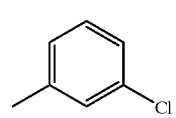

Id2

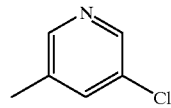

Id3

Id2: 3-chlorophenyl 6-acetoxymethyl-2-oxo-2H-1-benzopyran-3-carboxylate m.p.=152–154° C.; IR (KBr): 3066 (aromatic C—H), 1735 (C=O esters and lactone), 1628, 1579, 1474, 1367, 1249 cm$^{-1}$ Id3: 5-chloro-3-pyridyl 6-acetoxymethyl-2-oxo-2H-1-benzopyran-3-carboxylate m.p.=153–155° C.; IR (KBr): 3075 (aromatic C—H), 1783, 1773, 1728 (C=O esters and lactone), 1624, 1557, 1229, 1217 cm$^{-1}$

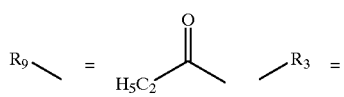

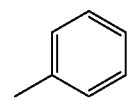

Id5

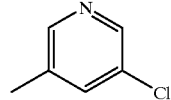

Id6

Id5: phenyl 6-propionyloxymethyl-2-oxo-2H-1-benzopyran-3-carboxylate m.p.=186–187° C.; IR (KBr): 3066 (aromatic C—H), 2982, 2942, 1733 (C=O esters and lactone), 1628, 1580, 1493, 1251, 1197 cm$^{-1}$ Id6: 5-chloro-3-pyridyl 6-propionyloxymethyl-2-oxo-2H-1-benzopyran-3-carboxylate m.p.=156–158° C.; IR (KBr): 3059, 3039 (aromatic C—H), 1779, 1761, 1732 (C=O esters and lactone), 1620, 1570, 1421, 1377, 1241, 1211, 1180, 1168 cm$^{-1}$

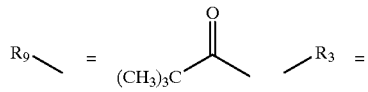

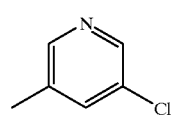

Id8

Id8: 5-chloro-3-pyridyl 6-trimethylacetoxymethyl-2-oxo-2H-1-benzopyran-3-carboxylate m.p.=175–177° C.

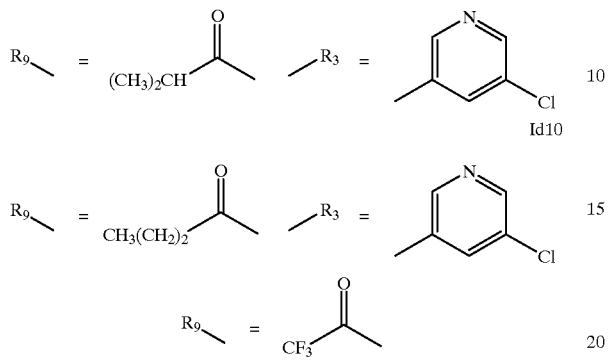

Id9: 5-chloro-3-pyridyl 6-dimethylacetoxymethyl-2-oxo-2H-1-benzopyran-3-carboxylate m.p.=162–164° C.; IR (KBr): 3078, 3024 (aromatic C—H), 2974, 1783, 1774, 1727 (C=O esters and lactone), 1625, 1577, 1229, 1221 cm$^{-1}$ Id10: 5-chloro-3-pyridyl 6-butyryloxymethyl-2-oxo-2H-1-benzopyran-3-carboxylate m.p.=146–148° C.; IR (KBr): 3066, 3037 (aromatic C—H), 2965, 1780, 1763, 1736 (C=O esters and lactone), 1621, 1572, 1215, 1168 cm$^{-1}$

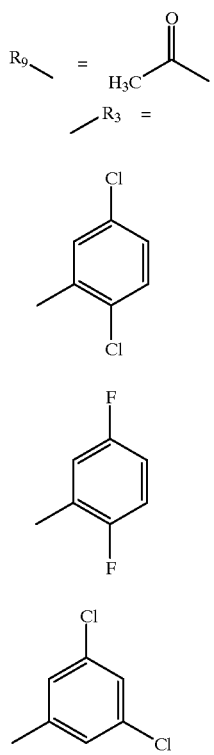

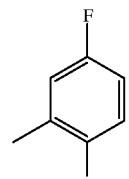

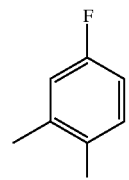

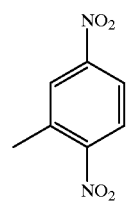

Id11: 2,5-dichlorophenyl 6-acetoxymethyl-2-oxo-2H-1-benzopyran-3-carboxylate m.p.=168–171° C.; IR (KBr): 3068, 3027, 1775, 1728, 1624, 1576, 1257, 1203 cm$^{-1}$ Id12: 2,5-difluorophenyl 6-acetoxymethyl-2-oxo-2H-1-benzopyran-3-carboxylate m.p.=137–139° C.; IR (KBr): 3061, 1776, 1723, 1626, 1576, 1511, 1264, 1251, 1239, 1213 cm$^{-1}$ Id13: 3,5-dichlorophenyl 6-acetoxymethyl-2-oxo-2H-1-benzopyran-3-carboxylate m.p.=146–150° C.; IR (KBr): 3087, 3068, 3050, 2961, 1770, 1723, 1623, 1583, 1248 cm$^{-1}$ Id14: 2-bromo-5-fluorophenyl 6-acetoxymethyl-2-oxo-2H-1-benzopyran-3-carboxylate m.p.=148–150° C.; IR (KBr): 3086, 1767, 1740, 1716, 1578, 1480, 1376, 1239, 1216 cm$^{-1}$ Id15: 5-fluoro-2-nitrophenyl 6-acetoxymethyl-2-oxo-2H-1-benzopyran-3-carboxylate m.p.=157–161° C.; IR (KBr): 3108, 3070, 1780, 1741, 1616, 1599, 1576, 1517, 1338, 1236, 1206 cm$^{-1}$ Id16: 2,5-dinitrophenyl 6-acetoxymethyl-2-oxo-2H-1-benzopyran-3-carboxylate m.p.=162–164° C.; IR (KBr): 3128, 3100, 3054, 1776, 1735, 1622, 1575, 1543, 1349, 1232, 1204 cm$^{-1}$ Series Ie Synthesis of Ethyl 6-phenylthiomethyl-2-oxo-2H-1-benzopyran-3-carboxylate (Ie1) (Intermediate)

A mixture of 1 g of ethyl 6-chloromethyl-2-oxo-2H-1-benzopyran-3-carboxylate (3.75 mmol), 0.57 g of potassium carbonate (4.13 mmol), 2.07 g of thiophenol (18.75 mmol) and 10 ml of absolute ethanol is reflux for 3 h. After removal of the solvent by distillation under reduced pressure, the residue is taken up in chloroform. The organic phase is washed with water and then dried over $MgSO_4$. The solvent is removed by distillation under reduced pressure and the residue is washed with hexane to remove the excess thiophenol. The title product is recrystallized from ethyl acetate/ petroleum ether.

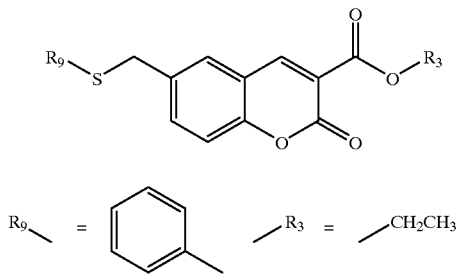

Ie1

Ie1: ethyl 6-phenylthiomethyl-2-oxo-2H-1-benzopyran-3-carboxylate m.p.=123–125° C.

Series If

Synthesis of Alkyl or Aryl 6-aminomethyl-2-oxo-2H-1-benzopyran-3-carboxylate Hydrochlorides (General Method) (If2, 3)

A mixture of 1 g of the appropriate 6-hexamethylenetetraammoniomethyl-2-oxo-2H-1-benzopyran-3-carboxylate chloride, 10 ml of ethanol and 0.5 ml of concentrated hydrochloric acid is placed on a boiling water bath for 15 min. After cooling, the insoluble material is removed by filtration. The filtrate solvent is removed by distillation under reduced pressure. The residue is taken up in 10 ml of 1% sodium bicarbonate solution. The insoluble material obtained is collected by filtration, washed with water and dried. If necessary, the precipitate is washed with ether or methanol.

Synthesis of Ethyl 6-aminomethyl-2-oxo-2H-1-benzopyran-3-carboxylate Hydrochloride (Special Case) (If1) (Intermediate)

A mixture of 1 g of ethyl 6-hexamethylenetetraammoniomethyl-2-oxo-2H-1-benzopyran-3-carboxylate chloride, 10 ml of absolute ethanol and 0.5 ml of concentrated hydrochloric acid is placed on a boiling water bath for 15 min. After cooling, the insoluble material is removed by filtration. The filtrate solvent is removed by distillation under reduced pressure. The residue obtained is taken up in 5 ml of water and the solution is washed twice with chloroform. 5 ml of an aqueous 2% solution of sodium carbonate are added to the aqueous phase. The mixture is extracted five times with 20 ml of chloroform. The combined organic phases are dried over $MgSO_4$. The solvent is removed by distillation under reduced pressure and the residue is taken up in methanol. Hydrogen chloride gas is bubbled into the methanolic solution for 15 min. Addition of ether causes precipitation of the title product, which is collected by filtration, washed with ether and dried.

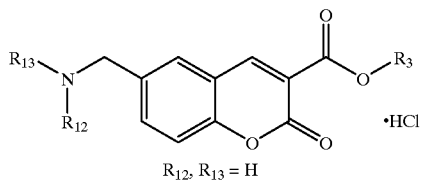

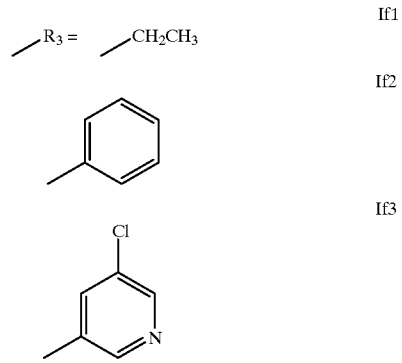

If1

If2

If3

If1: ethyl 6-aminomethyl-2-oxo-2H-1-benzopyran-3-carboxylate hydrochloride (intermediate)

m.p.=234–235° C.; IR (KBr): 2964, 2892, 1764 (C=O ester), 1747 (C=O lactone), 1624, 1579, 1381, 1258 cm$^{-1}$ If2: phenyl 6-aminomethyl-2-oxo-2H-1-benzopyran-3-carboxylate hydrochloride hemihydrate m.p.=250–251° C.

If3: 5-chloro-3-pyridyl 6-aminomethyl-2-oxo-2H-1-benzopyran-3-carboxylate hydrochloride m.p.=230° C., dec.

Series Ig

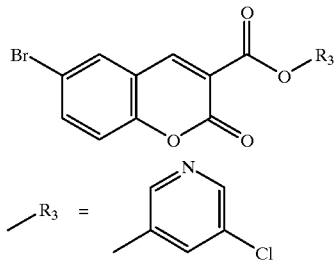

Ig1: 5-chloro-3-pyridyl 6-bromo-2-oxo-2H-1-benzopyran-3-carboxylate m.p.=228–230° C.

Series Ih

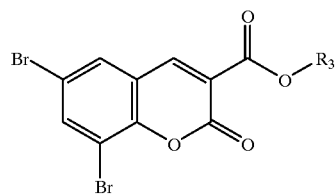

—R₃ = 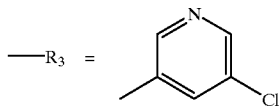

Ih1: 5-chloro-3-pyridyl 6,8-dibromo-2-oxo-2H-1-benzopyran-3-carboxylate m.p.=201–203° C.

Series Ii

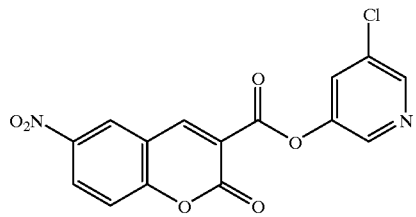

Ii1: 5-chloro-2-pyridyl 6-nitro-2-oxo-2H-1-benzopyran-3-carboxylate m.p.=287–289° C.; IR (KBr): 3075, 3049, 1782, 1730, 1615, 1569, 1542, 1371, 1347, 1249, 1212 cm$^{-1}$ Series Ij

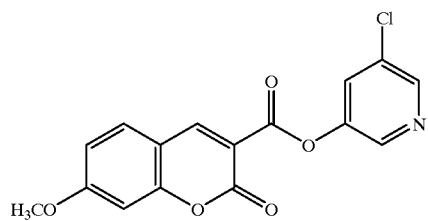

Ij1: 5-chloro-2-pyridyl 7-methoxy-2-oxo-2H-1-benzopyran-3-carboxylate m.p.=248–250° C.; IR (KBr): 3084, 3061, 1786, 1758, 1622, 1606, 1382, 1296, 1226, 1216 cm$^{-1}$ Series Ik

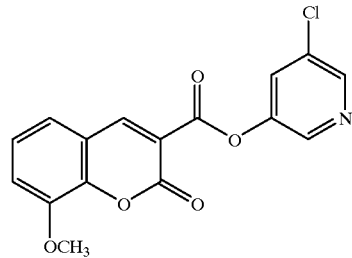

Ik1: 5-chloro-2-pyridyl 8-methoxy-2-oxo-2H-1-benzopyran-3-carboxylate m.p.=203–204° C.; IR (KBr): 3062, 3005, 1770, 1719, 1607, 1572, 1475, 1418, 1377, 1278, 1244, 1225 cm$^{-1}$ Series Il

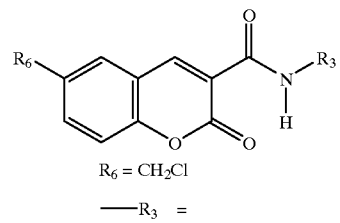

$R_6 = CH_2Cl$

—R₃ =

Il1 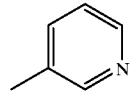

Il2 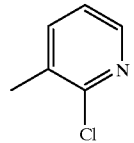

Il3

Il1: N-(3-pyridyl)-6-chloromethyl-2-oxo-2H-1-benzopyran-3-carboxamide m.p.=270° C., dec.

Il2: N-(2-chloro-3-pyridyl)-6-chloromethyl-2-oxo-2H-1-benzopyran-3-carboxamide m.p.=211° C., dec.

Il3: N-(6-methoxy-3-pyridyl)-6-chloromethyl-2-oxo-2H-1-benzopyran-3-carboxamide m.p.=225° C., dec.

Series III

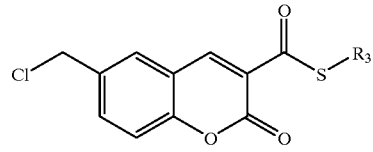

—R₃ =

III1 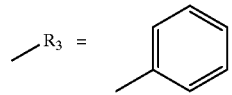

III2 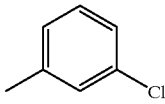

III1: S-phenyl 6-chloromethyl-2-oxo-2H-1-benzopyran-3-carbothioate m.p.=164–166° C.; IR (KBr): 3060, 3042 (aromatic C—H), 1724, 1655 (C=O thioester and lactone), 1568, 1178 cm$^{-1}$; NMR (CDCl₃/HMDS): δ(ppm) 4.55 (s, 2H, —CH$_2$Cl), 7.35 (bm, 6H, 8-H, 2'-H, 3'-H, 4'-H, 5'-H, 6'-H), 7.60 (s, 1H, 5-H), 7.65 (d, 1H, 7-H), 8.50 (s, 1H, 4-H)

III2: S-(3-chlorophenyl) 6-chloromethyl-2-oxo-2H-1-benzopyran-3-carbothioate m.p.=194–195° C.

Series IV

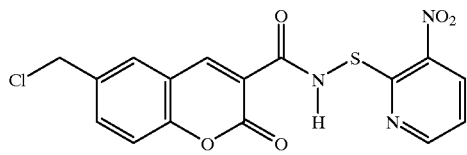

IV1: N-[(3-nitro-2-pyridyl)sulfanyl]-6-chloromethyl-2-oxo-2H-1-benzopyran-3-carboxamide m.p.=252–254° C.

Series V

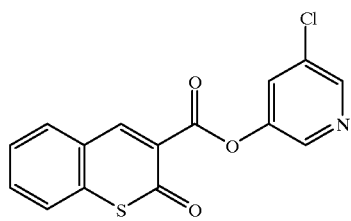

V1: 5-chloro-2-pyridyl 2-oxo-2H-1-benzothiopyran-3-carboxylate m.p.=174–176° C.; IR (KBr): 3043, 1737, 1714, 1648, 1593, 1547, 1422, 1279, 1212 cm$^{-1}$ Biological Results Experimental Protocols The inactivating or inhibitory properties of the coumarin derivatives were tested with respect to a certain number of enzymes: human leukocyte elastase, bovine α-chymotrypsin, human thrombin and bovine trypsin. The kinetic measurements were taken at 25° C. in the following buffers: 0.1 M Hepes, 0.5 M NaCl, 0.01% Tween 80, pH 8.0 (human leukocyte elastase); 0.025 M NaH$_2$PO$_4$, 0.05 M KCl, pH 7.5 (α-chymotrypsin); 0.01 M Tris, 0.01 M Hepes, 0.1 M NaCl, 0.1% PEG-6000, pH 7.5 (human thrombin); 0.1 M Tris, 0.01 M CaCl$_2$, pH 7.5 (bovine trypsin). The chromogenic substrates used to determine the activity of the enzymes are: MeOSuc-Ala$_2$-Pro-Val-pNA (human leukocyte elastase); Suc-Ala$_2$-Pro-Phe-pNA (α-chymotrypsin); H-D-Phe-Pip-Arg-pNA (human thrombin); N-benzoyl-Arg-pNA (bovine trypsin) (pNA: para-nitroaniline).

Characterization of the Inactivation Process

The interaction of a suicide substrate with a serine protease corresponds to the minimum reaction scheme described in equation 1 in which E represents the enzyme, I represents the inhibitor, E-I represents the acyl-enzyme and E-I' represents the inactivated enzyme [Silverman R. B., 1988, "Mechanism-based enzyme inactivation: chemistry and enzymology", volume 1 CRC Press, Boca Raton, Fla.]:

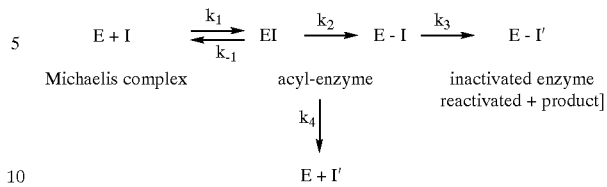

(equation 1)

Michaelis complex    acyl-enzyme    inactivated enzyme
                                    reactivated + product]

When $k_4$ is small compared to $k_3$, equation 1 can be simplified (equation 2, [Daniels et al., 1983, J. Biol. Chem., 258: 15046–15053]):

(equation 2)]

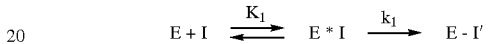

in which E*I represents both the species EI and E-I (kind of kinetic chimer)

For the study of the molecules which exhibit transient inactivation, the corresponding reaction scheme is the scheme of equation 1 for which $k_3$ is zero. Considering the first instants of the reaction, the system reduces to a simplified equation of the form of equation 2.

The kinetic constants characterizing the inactivation of the enzymes with the coumarin derivatives were determined using either the conventional sampling method (or batchwise method) or a method placing the inhibitor and the substrate in competition (or continuous method); these methods are described by Pochet et al. [Pochet et al., 1996, J. Med. Chem., 39: 2579–2585].

The inactivation of serine proteaaes with the coumarin derivatives is thus characterized by the following constants (see Eq. 2):

$K_I$: apparent dissociation constant of an enzyme-inhibitor complex located upstream of $k_i$ $k_i$: first-order rate constant for inactivation at infinite inhibitor concentration $k_i/K_I$: index of the overall inactivating efficacy of the inhibitor.

Biological Results

The coumarin derivatives lead to a definitive inactivation of α-chymotrypsin (α-CT), whereas the inactivation observed for human leukocyte elastase (HLE) and human thrombin is transient. Thus, the compound 5-chloro-3-pyridyl 6-methyl-2-oxo-2H-1-benzopyran-3-carboxylate (750 nM) inhibits HLE (100 nM) to an extent of 90% in less than one minute; the inhibition remains at 90% for 80 min and the half-reactivation time for the enzyme is 35 min. In the case of HLE and thrombin, the parameters $k_i/K_I$ given in Tables 1–5 correspond to the inactivation phase.

Whereas the phenyl esters, which are both in activators of α-CT, are essentially non-inactivators of HLE [Pochet et al., 1996 J. Med. Chem., 39: 2579–2585], the 2-pyridyl esters (Table 1) and 3-pyridyl esters (Table 2) can exhibit HLE-inhibitory activity.

In the absence of the chloromethyl substituent in position 6 of the coumarin ring (Table 3), the α-CT-inactivating power is lost, whereas the transient inactivation of human leukocyte elastase persists. Thrombin and trypsin are not inactivated. The molecules given in Table 3 thus act selectively on human leukocyte elastase.

Certain 2-pyridyl and 3-pyridyl esters inactivate human thrombin (Tables 1 and 2).

TABLE 1

$K_i/K_I$ or $k_{obs}/[I]$ $(M^{-1} \cdot s^{-1})$

| Y | α-CT | LHE | Thrombin | Trypsin |
|---|---|---|---|---|
| H | 1670 | 420 | ≈240 | N.I.[a] |
| 6-Cl | 107400 | 26000 | 7200 | — |
| 5-Cl | ≈2500 | 110 | N.I. | — |
| 6-CH$_3$ | 3300 | 200 | N.I. | N.I. |
| 4-CH$_3$ | 5950 | 300 | 3900 | N.I. |

[a]N.I.: non-inactivator

TABLE 2

$K_i/K_I$ or $k_{obs}/[I]$ $(M^{-1} \cdot s^{-1})$

| Y | α-CT | LHE | Thrombin | Trypsin |
|---|---|---|---|---|
| H | 15800 | 770 | N.I.[a] | N.I. |
| 6-CH$_3$ | ≈1000 | N.I. | N.I. | — |
| 5-Cl | 30970 | 64600 | ≈200 | N.I. |
| 2-Cl | 4300 | 3310 | — | — |
| 2-Br | 2750 | 3000 | — | — |
| 2-NO$_2$-6-CH$_3$ | ≈1500 | N.I. | — | — |
| 2-NO$_2$ | ≈4500 | ≈4000 | — | — |
| 5-CH$_3$ | ≈2500 | ≈1000 | N.I. | — |

[a]N.I.: non-inactivator

TABLE 3

$K_i/K_I$ or $k_{obs}/[I]$ $(M^{-1} \cdot s^{-1})$

| X | α-CT | LHE | Thrombin | Trypsin |
|---|---|---|---|---|
| H | N.I.[a] | 32850 | N.I. | N.I. |
| CH$_3$ | N.I. | 32500 | N.I. | N.I. |
| CH$_2$OCOCH$_3$ | N.I. | 107000 | N.I. | N.I. |
| CH$_2$OCOC$_2$H$_5$ | N.I. | 62000 | N.I. | N.I. |
| CH$_2$OCOCH(CH$_3$)$_2$ | N.I. | 45000 | N.I. | N.I. |
| CH$_2$OCO(CH$_2$)$_2$CH$_3$ | N.I. | 67600 | N.I. | N.I. |
| CH$_2$OCOC(CH$_3$)$_3$ | N.I. | 95500 | N.I. | N.I. |
| CH$_2$NH$_2$, HCl | N.I. | 9100 | N.I. | — |
| Br | N.I. | 58000 | — | — |

[a]N.I.: non-inactivator

TABLE 4

$K_i/K_I$ (M$^{-1}$·s$^{-1}$)

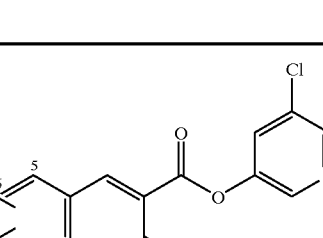

| Z | α-CT X, X' | LHE |
|---|---|---|
| O | 6,8-Br, Br | 54000 |
| O | 8-OCH$_3$ | 71500 |
| S | H | 15700 |

I

Phenyl ester coumarin derivatives exhibit inhibitory activity with respect to human thrombin. This is the case for compounds I, R$_1$=CH$_2$Cl, R$_2$=H (k$_{obs}$/[I]=500 M$^{-1}$.s$^{-1}$); I, R$_1$=CH$_2$Cl, R$_2$=m-Cl (k$_{obs}$/[I]=21000 M$^{-1}$.s$^{-1}$).

Other phenyl esters inactivate α-CT or thrombin efficiently. Their efficacies are given in Table 5. For the derivatives which have no chloromethyl substituent in position 6, a transient inactivation of α-CT may be observed, contrary to what is found for the pyridyl esters. In this case, the k$_i$/K$_I$ parameters correspond to the inactivation phase.

TABLE 5

$K_i/K_I$ or $k_{obs}$/[I] (M$^{-1}$·s$^{-1}$)

| X | Y | Y' | α-CT | HLE | Thrombin |
|---|---|---|---|---|---|
| CH$_2$Cl | o-NO$_2$ | H | 9300 | 1250 | — |
| CH$_2$Cl | m-OCH$_3$ | H | 188500 | 98 | — |
| CH$_2$Cl | m-CF$_3$ | H | <500 | 330 | — |
| CH$_2$Cl | m-OCH$_3$ | m'-Cl | 1200 | 350 | — |
| CH$_2$Cl | o-Cl | o'-Cl | N.I.[a] | <200 | N.I. |
| CH$_2$Cl | o-Cl | m-Cl | 1200 | <200 | N.I. |
| CH$_2$Cl | o-Cl | m'-Cl | 288000 | 2700 | 85700 |
| CH$_2$Cl | m-Cl | m'-Cl | 110000 | 4000 | N.I. |
| CH$_3$ | m-Cl | H | 9400 | 1100 | — |
| CH$_2$OCOCH$_3$ | m-Cl | H | 20000 | 1440 | 580 |
| H | o-Cl | m'-Cl | — | 5800 | N.I. |
| CH$_3$ | o-Cl | m'-Cl | — | 3000 | — |
| CH$_2$OCOCH$_3$ | o-Cl | m'-Cl | — | — | 500 |
| H | o-F | m'-F | — | — | N.I. |
| CH$_2$OCOCH$_3$ | o-F | m'-F | — | — | 150 |

TABLE 5-continued

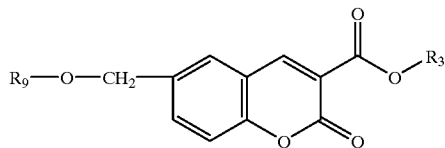

| | $K_i/K_I$ or $k_{obs}/[I]$ $(M^{-1} \cdot s^{-1})$ | | | | |
|---|---|---|---|---|---|
| X | Y | Y' | α-CT | HLE | Thrombin |
| $CH_2Cl$ | H | H | 39000 | N.I. | — |
| $CH_2Cl$ | m-Cl | H | 730000 | <200 | N.I. |

[a]N.I.: non-inactivator

What is claimed is:

1. A compound of the formula in which $R_3$ represents optionally substituted pyridyl and $R_9$ represents a lower alkanoyl radical selected from the group consisting of $CH_3$—C=(O)—, $C_2H_5$—C(=O)—, $(CH_3)_2$—CH—C(=O)—, $(CH_3)_3$—C—(C=(O)—, and $(CH_3)_2$—CH—C(=O)—.

2. Pharmaceutical composition, comprising at least one compound according to claim 1 in combination with a pharmaceutically acceptable vehicle.

3. A method of inhibiting activity of at least one of a serine protease and a cysteine protease in a patient in need of such treatment, comprising administering to said patient an effective amount of a compound according to claim 1.

* * * * *